US008618336B2

(12) United States Patent
Macht et al.

(10) Patent No.: US 8,618,336 B2
(45) Date of Patent: Dec. 31, 2013

(54) PROCESS FOR LONG-TERM OPERATION OF A HETEROGENEOUSLY CATALYZED PARTIAL GAS PHASE OXIDATION OF PROPENE TO ACROLEIN

(75) Inventors: Josef Macht, Mannheim (DE); Klaus Joachim Mueller-Engel, Stutensee (DE); Frank Rosowski, Mannheim (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 13/271,448

(22) Filed: Oct. 12, 2011

(65) Prior Publication Data

US 2012/0095267 A1 Apr. 19, 2012

Related U.S. Application Data

(60) Provisional application No. 61/393,370, filed on Oct. 15, 2010.

(30) Foreign Application Priority Data

Oct. 15, 2010 (DE) .................. 10 2010 048 405

(51) Int. Cl.
C07C 45/28 (2006.01)
(52) U.S. Cl.
USPC ............................ 568/449; 568/476; 568/479
(58) Field of Classification Search
USPC .................................................. 568/476, 479
See application file for complete search history.

(56) References Cited

U.S. PATENT DOCUMENTS

| 3,147,084 A | 9/1964 | Franzen et al. |
| 4,438,217 A | 3/1984 | Takata et al. |
| 7,019,168 B2 | 3/2006 | Dieterle et al. |
| 7,019,176 B2 * | 3/2006 | Dieterle et al. ............... 568/476 |
| 7,115,776 B2 | 10/2006 | Hammon et al. |
| 7,534,339 B2 | 5/2009 | Matsumoto et al. |

FOREIGN PATENT DOCUMENTS

| DE | 2 201 528 B1 | 11/1972 |
| DE | 28 30 765 A1 | 1/1980 |
| DE | 29 03 218 A1 | 8/1980 |
| DE | 29 09 671 A1 | 10/1980 |
| DE | 25 13 405 C2 | 10/1982 |
| DE | 33 00 044 A1 | 7/1983 |
| DE | 33 38 380 C2 | 10/1988 |
| DE | 40 23 239 A1 | 1/1992 |
| DE | 196 06 877 A1 | 8/1997 |
| DE | 196 27 847 A1 | 1/1998 |
| DE | 197 40 252 A1 | 3/1999 |
| DE | 197 46 210 A1 | 4/1999 |
| DE | 198 55 913 A1 | 6/2000 |
| DE | 199 02 562 A1 | 7/2000 |
| DE | 199 10 506 A1 | 9/2000 |
| DE | 199 10 508 A1 | 9/2000 |
| DE | 199 24 532 A1 | 11/2000 |
| DE | 199 55 176 A1 | 1/2001 |
| DE | 199 48 241 A1 | 4/2001 |
| DE | 199 48 248 A1 | 4/2001 |
| DE | 199 48 523 A1 | 4/2001 |
| DE | 199 55 168 A1 | 5/2001 |
| DE | 100 46 957 A1 | 4/2002 |
| DE | 100 63 162 A1 | 6/2002 |
| DE | 101 15 277 A1 | 6/2002 |
| DE | 101 01 695 A1 | 7/2002 |
| DE | 102 35 847 | 8/2003 |
| DE | 10 2004 025 445 A1 | 2/2005 |
| DE | 103 50 812 A1 | 6/2005 |
| DE | 103 51 269 A1 | 6/2005 |
| DE | 10 2004 008 573 A1 | 9/2005 |
| DE | 10 2007 005 606 A1 | 4/2008 |
| DE | 10 2007 004 961 A1 | 7/2008 |
| DE | 10 2008 040 093 A1 | 12/2008 |
| DE | 10 2008 040 094 A1 | 1/2009 |
| DE | 10 2008 042 060 A1 | 6/2009 |
| DE | 10 2009 047 291 A1 | 9/2010 |
| DE | 10 2010 048 405 A1 | 5/2011 |
| EP | 0 015 565 A1 | 9/1980 |
| EP | 0 279 374 A1 | 8/1988 |
| EP | 0 293 224 A1 | 11/1988 |
| EP | 0 293 859 A1 | 12/1988 |
| EP | 0 382 098 A2 | 8/1990 |
| EP | 0 383 224 A2 | 8/1990 |
| EP | 0 575 897 A1 | 12/1993 |
| EP | 0 468 290 B1 | 3/1994 |
| EP | 0 614 872 A1 | 9/1994 |
| EP | 0 700 714 A1 | 3/1996 |
| EP | 0 700 893 A1 | 3/1996 |
| EP | 0 714 700 A2 | 6/1996 |
| EP | 0 807 465 A1 | 11/1997 |
| EP | 0 873 783 A1 | 10/1998 |
| EP | 0 982 287 A1 | 3/2000 |
| EP | 0 982 288 A2 | 3/2000 |
| EP | 0 982 289 A2 | 3/2000 |
| EP | 1 106 598 A2 | 6/2001 |
| EP | 1 180 508 A1 | 2/2002 |
| EP | 1 270 065 A1 | 1/2003 |
| EP | 1 159 244 B1 | 10/2003 |

(Continued)

OTHER PUBLICATIONS

International Search Report issued Apr. 18, 2012, in PCT/EP2011/067887, filed Oct. 13, 2011 (with Translation of Category of Cited Documents).

*Primary Examiner* — Sikarl Witherspoon
(74) *Attorney, Agent, or Firm* — Oblon, Spivak, McClelland, Maier & Neustadt, L.L.P.

(57) ABSTRACT

A process for long-term operation of a heterogeneously catalyzed partial gas phase oxidation of propene to acrolein, in which the propene present in the reaction gas input mixture is partially oxidized as this gas mixture passes through the fixed catalyst bed which is accommodated in two spatially successive temperature zones A, B, and, in long-term operation, as a measure to counteract the reduction in the quality of the fixed catalyst bed, the temperature of at least one of the two temperature zones is increased such that the difference $T^B - T^A$ becomes increasingly greater, where $T^B$ is the temperature of temperature zone B, and $T^A$ the temperature of temperature zone A.

20 Claims, No Drawings

(56) References Cited

FOREIGN PATENT DOCUMENTS

| | | |
|---|---|---|
| EP | 1 547 944 A1 | 6/2005 |
| EP | 1 547 994 A1 | 6/2005 |
| EP | 1 577 001 A1 | 9/2005 |
| WO | WO 98/24746 A1 | 6/1998 |
| WO | WO 01/36364 A1 | 5/2001 |
| WO | WO 02/062737 A2 | 8/2002 |
| WO | WO 2004/007064 A1 | 1/2004 |
| WO | WO 2004/009525 A1 | 1/2004 |
| WO | WO 2004/085362 A1 | 10/2004 |
| WO | WO 2004/085363 A1 | 10/2004 |
| WO | WO 2004/085365 A2 | 10/2004 |
| WO | WO 2004/085367 A1 | 10/2004 |
| WO | WO 2004/085369 A1 | 10/2004 |
| WO | WO 2004/085370 A1 | 10/2004 |
| WO | WO 2005/009608 A1 | 2/2005 |
| WO | WO 2005/042459 A1 | 5/2005 |
| WO | WO 2005/082517 A1 | 9/2005 |
| WO | WO 2006/002703 A1 | 1/2006 |
| WO | WO 2006/002708 A1 | 1/2006 |
| WO | WO 2006/002713 A1 | 1/2006 |
| WO | WO 2007/013504 A1 | 2/2007 |
| WO | WO 2007/017431 A1 | 2/2007 |
| WO | WO 2007/042457 A1 | 4/2007 |
| WO | WO 2007/060036 A1 | 5/2007 |
| WO | WO 2007/082827 A1 | 7/2007 |
| WO | WO 2008/087115 A2 | 7/2008 |
| WO | WO 2008/087116 A1 | 7/2008 |

* cited by examiner

PROCESS FOR LONG-TERM OPERATION OF A HETEROGENEOUSLY CATALYZED PARTIAL GAS PHASE OXIDATION OF PROPENE TO ACROLEIN

The present invention relates to a process for long-term operation of a heterogeneously catalyzed partial gas phase oxidation of propene to acrolein, in which a reaction gas input mixture which comprises propene, molecular oxygen and at least one inert gas and comprises the molecular oxygen and the propene in a molar $O_2:C_3H_6$ ratio of $\geq 1$ is conducted through a fixed catalyst bed whose active material is at least one multimetal oxide comprising the elements Mo, Fe and Bi, with the proviso that the fixed catalyst bed is arranged in two spatially successive (and generally adjoining) temperature zones A, B (extends over two spatially successive temperature zones A, B), both the temperature $T^A$ of temperature zone A and the temperature $T^B$ of temperature zone B are a temperature in the temperature range from 280 to 420° C., the reaction gas input mixture flows through temperature zones A, B in the time sequence "first A" and "then B", temperature zone A extending up to a conversion $C^A$ of the propene present in the reaction gas input mixture in the range from 45 to 85 mol %, and the conversion of the propene increasing in temperature zone B to a value $C^B$ of $\geq 90$ mol %, in single pass of the reaction gas input mixture through the overall fixed catalyst bed, the selectivity of acrolein formation, based on propene converted, is $\geq 80$ mol %, the space velocity of propene present in the reaction gas input mixture on the fixed catalyst bed is $\geq 140$ l (STP) of propene/l of fixed catalyst bed·h, the temperatures $T^A$ and $T^B$ on completion of fresh charging of the fixed catalyst bed are such that the difference $\Delta T^{BA} = T^B - T^A > 0°$ C., then, with increasing operating time, in order to counteract the reduction in the quality of the fixed catalyst bed, at least one of the two temperatures $T^A$, $T^B$ is increased.

In this document, a diluent gas which is essentially inert under the conditions of the heterogeneously catalyzed gas phase partial oxidation of propene to acrolein (also referred to in this document as "inert gas") are understood to mean those diluent gases whose constituents, under the conditions of the heterogeneously catalyzed gas phase partial oxidation (or else partial gas phase oxidation)—each constituent considered alone—remain unchanged to an extent of more than 95 mol %, preferably to an extent of more than 97 mol % and more preferably to an extent of more than 99 mol %.

The space velocity of reaction gas mixture (e.g. reaction gas input mixture) on a fixed catalyst bed which catalyzes a reaction step is understood to mean the amount of reaction gas mixture in standard liters (=l (STP); the volume in liters that the corresponding amount of reaction gas mixture would occupy under standard conditions, i.e. at 0° C. and 1 atm (1013.25 hPa)) which is supplied to the fixed catalyst bed based on the (bed) volume of the bed thereof (→unit=l (STP)/l·h). The space velocity may also be based only on one constituent of the reaction gas mixture. In that case, it is the volume of this constituent in l (STP) which is supplied to the fixed catalyst bed, based on the volume of the bed thereof, per hour.

The reaction gas input mixture therefore comprises, inter alia, inert gas in order to keep the reaction gas mixture outside the explosion range.

The process, described at the outset of this document, for heterogeneously catalyzed partial gas phase oxidation of propene to acrolein over a freshly charged fixed catalyst bed (which means that no partial oxidation has yet been performed over the fixed catalyst bed; it comprises newly produced, freshly manufactured catalysts) is known in principle, for example, from WO 2004/085362 and from the prior art cited in the same WO.

It is of significance, inter alia, as the first oxidation stage in the preparation of acrylic acid by two-stage heterogeneously catalyzed gas phase oxidation proceeding from propene. Acrylic acid is an important monomer which finds use as such or in the form of its alkyl esters for production of, for example, polymers suitable as adhesives or water-absorbing polymers. Acrolein is an important intermediate.

The fixed catalyst bed has the task of causing the desired partial oxidation of propene to proceed preferentially, for example compared to the full oxidation of propene to carbon oxides and water.

The chemical reaction proceeds when the reaction gas mixture flows through the fixed catalyst bed, during the residence time of the reaction gas mixture therein.

The heterogeneously catalyzed partial gas phase oxidation of propene to acrolein proceeds with pronounced exothermicity. Owing to a variety of possible parallel and/or further reactions, with regard to a very substantially selective conversion of the propene to acrolein, the sole measure of additionally using the catalyst is normally insufficient. Instead, it is additionally required for a very selective performance of the heterogeneously catalyzed gas phase partial oxidation of propene to acrolein in the fixed catalyst bed, with the simultaneous aim of appropriate conversion of the propene, to control the profile of the reaction temperature or the profile of the temperature of the fixed catalyst bed (in the fixed catalyst bed) to a certain degree in flow direction of the reaction gas mixture (cf., for example, EP-A 700714).

According to the teachings of the prior art, it has generally been found to be advantageous in this regard, especially in the case of elevated propene velocities on the fixed catalyst bed, to pour a freshly charged fixed catalyst bed into two spatially successive temperature zones, the temperatures $T^A$ and $T^B$ of which are such that the difference $\Delta T^{BA} = T^B - T^A > 0°$ C., and to conduct the reaction gas input mixture comprising propene and the molecular oxygen and the at least one inert gas through the fixed catalyst bed in such a way that the reaction gas input mixture flows through temperature zones A, B in the time sequence "first A" and "then B", the length of temperature zone A being such that it extends up to a conversion $C^A$ of the propene present in the reaction gas input mixture (the gas mixture which is supplied to the fixed catalyst bed) in the range from 45 to 85 mol %, and the length of temperature zone B being such that the conversion of the propene in temperature zone B (in the course of passage of the reaction gas mixture through reaction zone B) is increased to a value $C^B$ of $\geq 90$ mol % (cf., for example, EP-A 1159244).

In practice, temperature zones A, B are generally implemented in such a way that the fixed catalyst bed is introduced into a reaction chamber (for example the interior of a (reaction) tube), around which, for reasons of temperature regulation (heat removal), a fluid (preferably liquid) heat carrier (a heat exchange medium) is conducted or passed (in and out) within two essentially separate sections A, B which are spatially successive (and generally adjoining) in flow direction of the reaction gas mixture, said heat carrier being in contact with the material shell of the reaction space (the wall of the reaction space) along the particular section A or B. The heat carrier conducted within section A is normally supplied with the temperature $T^A$, and the heat carrier conducted within section B is normally supplied with the temperature $T^B$. The total heat capacity of the heat carrier stream conducted is normally very much greater than the total heat capacity of the reaction gas mixture stream. With regard to the heat transfer coefficient (from the material shell to the fluid heat carrier), the procedure is as described implicitly in EP-A 700714 and explicitly in EP-A 1547994.

The temperature of a temperature zone is understood in the prior art, as also in this document, to mean the temperature of the part of the fixed catalyst bed (or part of the fixed bed catalyst charge) present in the temperature zone in the course of execution of the process according to the invention, but in the theoretical absence of the chemical heat of reaction.

This temperature normally corresponds essentially to that temperature with which the corresponding heat carrier flows into the particular temperature zone.

For example, and in a particularly simple manner in application terms, the fixed catalyst bed (the fixed bed catalyst charge) may be present (as a bed) in the catalyst tubes (reaction tubes) of what is called a two-zone tube bundle reactor, as described, for example, in DE-As 19910508, 19948523, 19910506 and 19948241, and in the documents WO 2004/085362, WO 2007/082827, WO 2004/085370, WO 2004/085369, WO 2004/085363, WO 2004/085365, WO 2004/007064 and WO 2004/085367, and in the secondary literature cited in the aforementioned documents.

A preferred variant of a two-zone tube bundle reactor usable in accordance with the invention is disclosed by DE-C 2830765. However, the two-zone tube bundle reactors disclosed in DE-C 2513405, U.S. Pat. No. 3,147,084, DE-A 2201528, EP-A 383224 and DE-A 2903218 are also suitable for performance of the relevant procedure.

In other words, in a simple manner, the fixed bed catalyst charge for use in accordance with the invention is present in the reaction tubes of a multiple catalyst tube fixed bed reactor (tube bundle reactor), and two essentially spatially separate temperature control media (fluid heat carriers, heat exchange media), for example ionic liquids, water (steam), salt melts or liquid metals are conducted (passed; in and out) around the reaction tubes. The tube section over which the particular salt bath or metal bath extends represents a temperature zone.

Corresponding temperature zones can also be set up in thermoplate reactors, as disclosed, for example, by WO 2005/009608, or in heat exchanger plate reactors, as described, for example, by EP-A 1577001.

In addition to the above-described external measures for temperature control, the inert diluent gases which have already been mentioned, are used as part of the reaction gas input mixture and are capable of absorbing heat of reaction released with their heat capacity (internal measures for temperature control) contribute to the control of the reaction temperature profile in the fixed catalyst bed.

One of the most frequently used inert diluent gases is molecular nitrogen, which is employed automatically whenever the oxygen source used for the heterogeneously catalyzed gas phase partial oxidation is air.

Another frequently used inert diluent gas is steam, due to its general availability and advantageous molar heat capacity.

Other typically used inert diluent gases are noble gases (e.g. He, Ar, Ne), or the carbon oxides $CO_2$ and/or CO.

Useful inert gases with comparatively high molar heat capacity for the heterogeneously catalyzed partial gas phase oxidation of propene to acrolein also include saturated hydrocarbons, for example n-propane and ethane. In many cases, cycle gas is also used as inert diluent gas (cf. EP-A 1180508). The cycle gas refers to the residual gas which remains after a single-stage or multistage (the heterogeneously catalyzed partial oxidation of propene to acrolein can, for example, also be employed as only the first reaction stage of a two-stage heterogeneously catalyzed partial oxidation of propene to acrylic acid) heterogeneously catalyzed gas phase partial oxidation of propene to acrolein or acrylic acid when the target product (acrolein or acrylic acid) has been removed from the product gas mixture more or less selectively (for example by absorption into a suitable solvent, or by fractional condensation, or by a superimposition of absorption and condensation) (cf., for example, WO 2007/082827, page 6 ff).

In general, it consists predominantly of the inert diluent gases used for the partial oxidation, and of steam which is typically formed as a by-product in the partial oxidation or added as a diluent gas, and carbon oxides formed by unwanted full oxidation as a side reaction. In some cases, it still comprises small amounts of molecular oxygen unconsumed in the partial oxidation (residual oxygen) and/or of unconverted propene and/or unconverted acrolein intermediate.

In spite of the external and internal measures described for controlling the reaction temperature or the temperature of the fixed catalyst bed (the two aforementioned temperatures are essentially identical), the temperatures of temperature zones A, B are normally different from the reaction temperature which exists in each case along the fixed catalyst bed in flow direction (=the particular temperature of the reaction gas mixture) or the effective temperature of the fixed catalyst bed present in each case (it corresponds essentially to the reaction temperature present at the same level). The effective temperature of the fixed catalyst bed is the actual temperature of the fixed catalyst bed, which includes both the influence of the fluid heat carrier conducted outside the reaction space and the heat of reaction of the partial oxidation (whereas the term "temperature of the temperature zone", as already stated, excludes the influence of the heat of reaction of the partial oxidation). In contrast to the effective temperature of the fixed catalyst bed in flow direction along it, the temperature of a temperature zone is normally essentially constant. When the temperature of a temperature zone is not completely constant, the term "temperature of a temperature zone" here means the (numerical) mean of the temperature over the temperature zone. The temperatures of the individual temperature zones are controlled essentially independently of one another. Normally, the effective temperature of the fixed catalyst bed at the particular bed level is greater than the temperature of the corresponding temperature zone.

It is significant in the aforementioned context that the temperature of the reaction gas mixture (and hence also the effective temperature of the fixed catalyst bed) in the course of passage through the fixed catalyst bed in flow direction of the reaction gas mixture in the particular temperature zone typically passes through a maximum value or declines proceeding from such a maximum value (what is called the hotspot value $T^{maxA}$ (in temperature zone A) or $T^{maxB}$ (in temperature zone B)). The difference between the hotspot value and the temperature of the corresponding temperature zone is referred to as the hotspot expansion $\Delta T^{HB}_A$ (in temperature zone A) or $\Delta T^{HB}_B$ (in temperature zone B).

One cause of this is the fact that the reactant concentration in the reaction gas mixture is at its highest at the entrance (inlet) of the reaction gas mixture into the fixed catalyst bed, which causes particularly high reaction rates there, which are accompanied by particularly high evolution of heat of reaction per unit time (on entry into the fixed catalyst bed, the reaction gas mixture (=the reaction gas input mixture) generally has essentially the temperature of temperature zone A).

Another cause of this is the finite heat transfer from the reaction gas mixture to the heat carrier.

According to the teaching of the prior art, in the freshly charged fixed catalyst bed, the general process conditions are generally selected advantageously such that $T^{maxA}-T^{maxB} \geq 0°$ C. (cf. WO 2004/085362, WO 2004/085370 and WO 2004/085363).

In addition, according to the teachings of the prior art cited, in the freshly charged fixed catalyst bed, the general process conditions are normally selected such that both $\Delta T^{HB}_B$ and $\Delta T^{HB}_A$ generally do not exceed 90° C. Usually, these temperature differences are $\geq 3°$ C. and $\leq 80°$ C., or $\leq 70°$ C., frequently $\geq 5°$ C. and $\leq 60°$ C., or $\leq 50°$ C. Appropriately in application terms, $\Delta T^{HB}_A$ is 40 to 90° C., or 40 to 80° C.

In addition, in the freshly charged fixed catalyst bed, (preferably at the same time) the change in $\Delta T^{HB}_A$ or $\Delta T^{HB}_B$ when the temperature of the corresponding temperature zone is increased by +1° C. is normally (cf. the prior art documents acknowledged) $\leq +9°$ C., preferably $\leq +7°$ C. or $\leq +5°$ C. or $\leq +3°$ C., but $>+0°$ C. (cf., for example, EP-A 1106598).

The positioning both of $T^A$ and $T^B$ within the temperature range from 280° C. to 420° C. ensures economic propene conversions (typically $\geq 90$ mol %) in single pass of the reaction gas mixture through the fixed catalyst bed (especially through the freshly charged fixed catalyst bed).

The working pressure in the heterogeneously catalyzed partial gas phase oxidation of propene to acrolein over the fixed catalyst bed may be either below 1 atm ($=1.0133 \cdot 10^5$ Pa) or above 1 atm. In general, it is within the range from $\geq 1$ to 20, or to 10 atm, or to 5 atm. A working pressure of 100 atm is typically not exceeded.

The catalysts of the fixed catalyst bed for the heterogeneously catalyzed partial gas phase oxidation of propene to acrolein generally have, as an active material, at least one multimetal oxide comprising the elements Mo, Fe and Bi (cf., for example, WO 2004/085362).

It is common knowledge that a gas phase partial oxidation of propene to acrolein with heterogeneous catalysis as described at the outset, on completion of fresh charging of the reactor with a fresh fixed catalyst bed, can be operated essentially continuously and over a prolonged period under essentially unchanged conditions while keeping the fixed catalyst bed (i.e. without exchanging the fixed catalyst bed, over one and the same fixed catalyst bed).

However, the fixed catalyst bed normally loses quality with increasing operating time (cf., for example, DE-A 102004025445). In general, the volume-specific activity in particular of the fixed catalyst bed worsens (under otherwise unchanged process conditions, the propene conversion based on a single pass of the reaction gas mixture through the fixed catalyst bed decreases with increasing operating time, which reduces the planned space-time yield in an acrolein production plant of acrolein or of acrolein and acrylic acid). Frequently, the selectivity of acrolein formation or of the overall target product formation of acrolein and acrylic acid also suffers.

EP-A 1106598 and DE-A 10351269 attempt to take account of the aforementioned evolution in the long-term operation of the heterogeneously catalyzed gas phase partial oxidation of propene to acrolein by gradually increasing the temperature of the temperature zone in which the fixed catalyst bed is present, and with it the temperature of the fixed catalyst bed, under otherwise substantially constant operating conditions, in order to essentially maintain the propene conversion in single pass of the reaction gas mixture through the fixed catalyst bed (in this case, it is possible, as recommended, for example, by WO 2004/085369, DE-A 10351269, DE-A 10350812 and EP-A 614872, to additionally counteract the reduction in quality of the fixed catalyst bed in long-term operation in the meantime by regenerating the fixed catalyst bed from time to time; for this purpose, the process for heterogeneously catalyzed fixed bed gas phase partial oxidation of propene to acrolein (or to acrolein and acrylic acid) is interrupted and, for example, a hot mixture of molecular oxygen and inert gas is conducted through the fixed catalyst bed; in this way, it is possible to reverse a reversible component of the reduction in quality (in aging) of the fixed catalyst bed). Such a regeneration can also be effected according to DE-A 102004008573, or WO 05/082517. For example, such a regeneration can be performed whenever the partial oxidation is interrupted, for example, because the reaction gas mixture has inadvertently assumed a composition which may be controllable only with difficulty with respect to explosion.

However, a disadvantage of the teachings of EP-A 1106598 and of DE-A 10351269 is that they suggest a synchronous increase in the temperature in the two temperature zones A, B. In other words, $T^A$ and $T^B$ are each increased to the same extent (by the same number of ° C.).

Such a procedure is advantageous over a procedure without an increase in the temperature of the fixed catalyst bed, and can also be employed advantageously in principle in the heterogeneously catalyzed partial oxidation of propene to acrolein (or to acrolein and acrylic acid) described at the outset of this document.

However, it is disadvantageous in that, although it ensures that the target propene conversion (based on single pass of the reaction gas mixture through the fixed catalyst bed) is maintained under otherwise unchanged operating conditions, this is normally at the cost of a reduced selectivity of acrolein formation or of overall target product formation of acrolein and acrylic acid (cf. WO 2007/082827).

WO 2007/082827 therefore recommends performing the long-term operation of a heterogeneously catalyzed partial gas phase oxidation of propene to acrolein as described at the outset (this is always also a gas phase partial oxidation of propene to acrolein and acrylic acid) in such a way that, in order to counteract the reduction in quality of the fixed catalyst bed, the temperature of temperature zone A, which at first (on completion of fresh charging of the fixed catalyst bed) had a lower temperature than temperature zone A, is increased with increasing operating time, and at the same time the temperature of temperature zone B is evolved further such that the difference $\Delta T^{BA}=T^B-T^A$ between the temperatures of the two temperature zones $T^A$, $T^B$ decreases with increasing operating time and possibly even changes sign (from + to −).

However, a disadvantage of the teaching of WO 2007/082827 is that the long-term mode of operation recommended therein prematurely impairs the service life of the fixed catalyst bed. In other words, it leads to a comparatively marked acceleration in the irreversible aging of the fixed catalyst bed. When the degree of irreversible aging of the fixed catalyst bed reaches the point from which, even in the case of a further increase in the temperature of the fixed catalyst bed, the conversion of propene based on a single pass of the reaction gas mixture through the fixed catalyst bed can no longer be maintained, or at best at the cost of a significant reduction in selectivity of acrolein formation or of overall target product formation of acrolein and acrylic acid, the fixed catalyst bed has to be replaced at least partly (cf. DE-A 10232748) or fully by a fresh fixed catalyst bed for reasons of the economic viability of the process. This time is referred to as the end of the service life of the fixed catalyst bed.

It was therefore an object of the present invention to provide an improved process for long-term operation of a heterogeneously catalyzed partial gas phase oxidation of propene to acrolein performed in two temperature zones as described at the outset of this document, which ensures, coupled with an improved service life of the fixed catalyst bed over the operating time, also a satisfactory selectivity of acrolein formation or of overall target product formation of acrolein and acrylic acid.

Accordingly, a process is provided for long-term operation of a heterogeneously catalyzed partial gas phase oxidation of propene to acrolein (this is always also a gas phase partial oxidation of propene to acrolein and acrylic acid), in which a reaction gas input mixture which comprises propene, molecular oxygen and at least one inert gas and comprises the molecular oxygen and the propene in a molar $O_2:C_3H_6$ ratio of $\geq 1$ is conducted through a fixed catalyst bed whose active material is at least one multimetal oxide comprising the elements Mo, Fe and Bi, with the proviso that the fixed catalyst bed is arranged in two spatially successive temperature zones A, B, both the temperature $T^A$ of temperature zone A and the temperature $T^B$ of temperature zone B are a temperature in the temperature range from 280 to 420° C., the reaction gas input mixture flows through temperature zones A, B in the time sequence "first A" and "then B", temperature zone A extending up to a conversion $C^A$ of the propene present in the reaction gas input mixture in the range from 45 to 85 mol %, and the conversion of the propene increasing in temperature zone B to a value $C^B$ of $\geq 90$ mol %, in single pass of the reaction gas input mixture through the overall fixed catalyst bed, the selectivity of acrolein formation, based on propene converted, is $\geq 80$ mol %, the space velocity of propene present in the reaction gas input mixture on the fixed catalyst bed is 140 l (STP) of propene/l of fixed catalyst bed·h, the temperatures $T^A$ and $T^B$ on completion of fresh charging of the fixed catalyst bed are such that the difference $\Delta T^{BA}=T^B-T^A>0°$ C., and then, with increasing operating time, in order to counteract the reduction in the quality of the fixed catalyst bed, at least one of the two temperatures $T^A$, $T^B$ is increased, wherein the increasing of the at least one of the two temperatures $T^A$, $T^B$ is undertaken such that the difference $\Delta T^{BA}=T^B-T^A$ increases with increasing operating time.

Advantageously, the difference $\Delta T^{BA}=T^B-T^A$ for the performance of the process according to the invention over the freshly charged fixed catalyst bed (i.e. at the start of the process according to the invention) will be $\geq 2°$ C., preferably $=3°$ C. and more preferably $=5°$ C. Typically, the difference $\Delta T^{BA}$ for the performance of the process according to the invention over the freshly charged fixed catalyst bed is $=50°$ C. and preferably $=40°$ C.

Differences $\Delta T^{BA}=T^B-T^A$ favorable in accordance with the invention for the performance of the process according to the invention over the freshly charged fixed catalyst bed are in the range of $=5°$ C. and $=35°$ C., or $=5°$ C. and $=30°$ C., or $=5°$ C. and $=25°$ C., or $=10°$ C. and $=25°$ C. or $=15°$ C. and $=20°$ C.

In general, the establishment of the above differences $\Delta T^{BA}$ for the performance of the process according to the invention over the freshly charged fixed catalyst bed (i.e. at the start of the process according to the invention) is associated with a difference $T^{maxA}-T^{maxB}$ which is $=0°$ C. and $=80°$ C., or $=70°$ C.

Appropriately in application terms, in the performance of the process according to the invention over the freshly charged fixed catalyst bed, the aim is that the difference $T^{maxA}-T^{maxB}$ is not too significant.

Favorable differences $T^{maxA}-T^{maxB}$ in the performance of the process according to the invention over the freshly charged fixed catalyst bed (i.e. at the start of the process according to the invention) are therefore $=1°$ C. and $=60°$ C., or $=50°$ C., preferably $=2°$ C. and $=40°$ C., advantageously $=3°$ C. and $=30°$ C., particularly advantageously $\geq 5°$ C. or $\geq 10°$ C. and $\leq 25°$ C., and most preferably $\geq 5°$ C. and $\leq 20°$ C. or $\leq 15°$ C.

A characteristic feature of the inventive procedure is that, in the long-term operation of the heterogeneously catalyzed partial gas phase oxidation of propene to acrolein over the same fixed catalyst bed, in order to counteract the reduction in the quality of the fixed catalyst bed, at least one of the two temperatures $T^A$, $T^B$ is increased with the proviso that the difference $\Delta T^{BA}=T^B-T^A$ increases with increasing operating time.

In other words, in accordance with the invention, the procedure should be such that, based in each case on the same operating time, $T^B$ in long-term operation undergoes a greater increase than $T^A$.

Expressed in other words, both $T^B$ and $T^A$ can be increased in the inventive long-term operation.

Advantageously in accordance with the invention, the increase in $T^B$ is 1.2 to 5 times the increase in $T^A$, based in each case on the same operating time in long-term operation of the process according to the invention.

In other words, favorable processes according to the invention are those in which the increase in $T^B$ is 1.5 to 4 times, or 1.5 to 3 times (for example twice), the increase in $T^A$, based in each case on the same operating time in long-term operation of the process according to the invention.

The consequence of the inventive procedure is normally that the difference $T^{maxA}-T^{maxB}$ also decreases with increasing operating time (compared to the difference value $T^{maxA}-T^{maxB}$ on completion of fresh charging of the fixed catalyst bed).

However, it has been found to be advantageous in accordance with the invention to avoid $T^{maxA}-T^{maxB}$ assuming negative values in long-term operation of the process according to the invention. However, the inventive procedure does not rule out that the difference $T^{maxA}-T^{maxB}$ becomes "negative". Appropriately in accordance with the invention, the procedure will therefore generally be such that the difference $T^{maxA}-T^{maxB}$ in long-term operation has a positive sign for as long as possible (for example within an operating time of at least 6 months, preferably within an operating time of at least 12 months, advantageously within an operating time of at least 18 months, particularly advantageously within an operating time of at least 24 months, even better within an operating time of at least 30 months, or of at least 36 months or more).

At this point, it should be emphasized that the temperatures of temperature zones A and B ($T^A$ and $T^B$) in industrial scale operation, for different reasons, may be subject to certain variations (generally within the range of $\pm 20°$ C. or $\pm 10°$ C.) (for example when an intermediate regeneration according to DE-A 10351269 is undertaken; immediately after completion of intermediate regeneration (compared to operation immediately before the intermediate regeneration), generally lower temperatures (in individual cases, this temperature difference may also be up to 40° C. or more) of the temperature zones are sufficient in order to ensure the same propene conversion based on single pass of the reaction gas mixture through the fixed catalyst bed under otherwise unchanged conditions). In this case, the actual profile of the temperature of the particular zone is plotted against time, and a fitted curve is drawn through the measurement points according to the least mean squares method developed by Legendre and Gauss. When the inventive features are fulfilled on the basis of these fitted curves, use is made of the inventive procedure.

In the case that, in the course of an inventive heterogeneously catalyzed gas phase partial oxidation of propene to acrolein (this is always also one of propene to acrolein and acrylic acid), due to, for example, changes in market demand or other changes in boundary conditions in the course of the long-term operation of one and the same fixed catalyst bed, process parameters such as the propene velocity on the fixed catalyst bed, or the propene velocity on the fixed catalyst bed and the propene conversion based on a single pass of the reaction gas mixture through the fixed catalyst bed, for example, are altered with a direct knock-on effect (such a change would also be an increase in the working pressure according to DE-A 10 2004 025445) on the temperature of temperature zones A, B, in order to essentially maintain them thus unchanged in the subsequent further operation over a prolonged period of time (operating section), an inventive procedure is also present when the inventive characterizing features are fulfilled in this subsequent prolonged operating section with reference to the fixed catalyst bed and the operation thereof essentially "directly" after the aforementioned change as the operation of a "fresh fixed catalyst bed". Propene velocities on the fixed catalyst bed within a range of (X±10) l (STP)/l·h are considered for the inventive purposes to be one and the same propene velocity. An inventive procedure is also present when the long-term operation at propene velocities on the fixed catalyst bed are 140 l (STP) of propene/l of fixed catalyst bed·h is temporarily interrupted by low-load operation (propene velocity on the fixed catalyst bed <140 l (STP)/l·h) and, when the low-load operating phases are ended, the result is an inventive high-load long-term operating pattern.

In addition, the process for heterogeneously catalyzed partial gas phase oxidation of propene to acrolein over the freshly charged fixed catalyst bed shall also be understood to mean the execution of the process after completion of any forming of the fixed catalyst bed which occurs, i.e. after attainment of the quasi-steady operating state.

Generally, use is also made of the process according to the invention by anyone who operates the process according to the invention only over a particular time range of the long-term operation and leaves the inventive long-term operating mode prior to the partial or full replacement of the fixed catalyst bed by a fresh bed.

Preferably in accordance with the invention, $\Delta T^{BA}$ in the long-term operation of the process according to the invention will not exceed 70° C. Particularly advantageously, $\Delta T^{BA}$ in the long-term operation of the process according to the invention will not exceed 60° C., and very particularly advantageously 50° C.

Processes particularly favorable in accordance with the invention are those in which $\Delta T^{BA}$ over the entire operating time of the long-term operation is in the range of 10° C. to 50° C., preferably in the range of 15° C. to 45° C., and most preferably in the range of 20° C. to 40° C.

Processes according to the invention are, for example, those processes in which $\Delta T^{BA}$ increases with increasing operating time by at least 5° C., or by at least 10° C., or by at least 15° C., or by at least 20° C., or by at least 25° C., or by at least 30° C. In general, $\Delta T^{BA}$ in the process according to the invention will increase by not more than 50° C., usually by not more than 30° C., frequently by not more than 20° C.

Frequently, in the inventive long-term operation, the temperature $T^A$ will vary over the entire operating time within the range from 300 to 400° C., and preferably within the range from 310° C. to 390° C. or within the range from 320° C. to 380° C.

In addition, in the inventive long-term operation, the temperature $T^B$ will vary over the entire operating time frequently within the range from 305° C. to 415° C., preferably within the range from 315° C. to 410° C. and more preferably within the range from 330° C. to 410° C.

Based on a single pass of the reaction gas mixture through the fixed catalyst bed, the conversion of propylene which results in temperature zone A in the inventive long-term operation over the entire operating time will advantageously be 50 to 80 mol % and particularly advantageously 55 to 75 mol %.

In temperature zone B, the conversion of propene based on a single pass of the reaction gas mixture in the inventive long-term operation, over the entire operating time, advantageously in accordance with the invention, will increase to a value of ≥92 mol %, or ≥94 mol %, preferably ≥96 mol % and most preferably ≥97 mol %, or ≥98 mol %, or ≥99 mol %.

In general, the long-term operation of the process according to the invention will extend to at least 2 operating months, or to at least 4 operating months, or at least 6 operating months, or at least 9 operating months, or at least 1 operating year, or at least 1.5 operating years, or at least 2 operating years, or at least 2.5 operating years, or at least 3 operating years, and in some cases even to at least 5 operating years, or at least 7 operating years and in particular cases even to 10 operating years or more.

The rate of change in $T^B$ averaged over an operating time of 1000 days may, in the process according to the invention, for example, be +0.04° C./day, while at the same time the rate of change in $T^A$ averaged over the same operating time is only +0.02° C./day.

In general, use of the process according to the invention will be commenced no later than when the fixed catalyst bed is in such a state that $C^B$ under otherwise unchanged process conditions is at least 0.2, or at least 0.3, or at least 0.4 or at least 0.5 mole percent lower than the value for $C^B$ under the same process conditions over the fresh fixed catalyst bed.

The catalysts and other process conditions for use for the process according to the invention will otherwise, appropriately in application terms, be selected such that the selectivity of acrolein formation, based on the propene converted in single pass of the reaction gas mixture through the fixed catalyst bed, is advantageously ≥82 mol %, or ≥84 mol %, or ≥87 mol %, or ≥89 mol %, or ≥90 mol %, or ≥92 mol %, or ≥94 mol %.

Typically, in the inventive procedure, acrylic acid is formed as a by-product (based on the molar amount of acrolein formed, generally in amounts of ≤15 mol % or ≤10 mol %). The latter is a welcome by-product especially when the process according to the invention forms the first reaction stage of a two-stage process for heterogeneously catalyzed partial gas phase oxidation of propene to acrylic acid. If acrolein and acrylic acid are therefore combined as the (joint) overall target product, the catalysts and other process conditions to be used for the process according to the invention will, appropriately in application terms, be selected such that the selectivity of overall target product formation, based on the propene conversion it single pass of the reaction gas mixture through the fixed catalyst bed, is ≥93 mol %, or ≥95 mol %, or ≥96 mol %, or ≥97 mol %, or ≥98 mol %.

Appropriately in application terms, the process according to the invention is preferably performed in the two-zone multiple catalyst tube reactors already addressed. The radial temperature gradient of the heat carrier within a temperature zone is generally 0.01 to 5° C., frequently 0.1 to 2° C., and advantageously in accordance with the invention is very low.

The flow rate of the heat carrier is generally selected, following the teaching of EP-A 700714, such that the temperature of the heat carrier from the entrance into the temperature zone to the exit from the temperature zone (as a result of the exothermicity of the reaction) rises by 0 to 15° C. Typically, the aforementioned $\Delta T$ will, in accordance with the invention, be 1 to 10° C., or 2 to 8° C., or 3 to 6° C. Advantageously, $\Delta T$ is small.

In principle, the process according to the invention can, however, also be performed in other reactors which have two temperature zones and are of the indirect heat exchanger type.

The inventive procedure is advantageous over the procedures recommended in the prior art especially when the propene velocity on the fixed catalyst bed is $\geq 150$ l (STP)/l·h, or $\geq 160$ l (STP)/l·h, or $\geq 170$ l (STP)/l·h, or $\geq 180$ l (STP)/l·h, or $\geq 190$ l (STP)/l·h, or $\geq 200$ l (STP)/l·h. In general, the propene velocity on the fixed catalyst bed in the process according to the invention will, however, be $\leq 600$ l (STP)/l·h, usually $\leq 400$ l (STP)/l·h, or $\leq 300$ l (STP)/l·h, or $\leq 250$ l (STP)/l·h.

The reason why the inventive procedure is advantageous, with regard to the selectivity of the acrolein formation or of the acrolein and acrylic acid formation (the overall target product formation), and with regard to the propene conversion which is established in single pass of the reaction gas mixture through the fixed catalyst bed, and with regard to the resulting service life of the fixed catalyst bed, is probably because the exothermicity of a heterogeneously catalyzed partial gas phase oxidation of propene to acrolein is comparatively high (340 kJ/mol).

At the propene velocities on the fixed catalyst bed required in accordance with the invention, and the propene conversions within the fixed catalyst bed which are required in a single pass of the reaction gas mixture through the fixed catalyst bed, this leads to the release of considerable heats of reaction.

In order to rule out any need for the acrolein formed in temperature zone A to pass through, in temperature zone B, excessively high effective fixed bed temperatures which promote unwanted full combustion of the acrolein, a considerable proportion of the propene conversion necessarily has to proceed in temperature zone A, which leads to the development of a pronounced hotspot temperature therein.

If, in long-term operation, the teaching of WO 2007/082827 is followed and $T^A$ is increased to a greater extent than $T^B$ over the operating time, as required by WO 2007/082827, effective catalyst bed temperatures which are prohibitive for the catalyst quality are obviously attained comparatively rapidly at least in some regions of temperature zone A. This reduces the catalyst quality to an increasingly irreversible degree with increasing operating time, which, moreover, in the event of a further increase in the fixed catalyst bed temperature, results at the same time in a considerable increase in the proportion of unwanted full combustion in temperature zone A. The ultimate result of this is that, at a comparatively early stage, propene conversion and/or selectivity of acrolein formation or of acrolein and acrylic acid formation (i.e. the target product yield $Y^{AC}$ or $Y^{AC+AA}$) can no longer be maintained even with the measure of an increasing increase in the temperature of the fixed catalyst bed, such that a partial or full exchange of the fixed catalyst bed is appropriate.

An early indicator for the early onset of the behavior just described is frequently the course of $\Delta T^{HB}_A$ against time. While $\Delta T^{HB}_A$ for the freshly charged fixed catalyst bed generally increases at first with increasing operating time and increase in $T^A$, in the case of employment of the procedure according to WO 2007/082827 in long-term operation the time from which $\Delta T^{HB}_A$ decreases on continuation of operation often sets in at a comparatively early stage. The onset of this decrease is normally a significant pointer for already pronounced irreversible damage to the fixed catalyst bed.

With the aid of the inventive procedure, the scenario described above can obviously be countered in a comparatively better manner.

In other words, the condition $T^{maxA} - T^{maxB} \geq 0$ alone is a necessary but insufficient condition for a successful long-term mode of operation. Particularly advantageous results are instead established when the highest effective temperature of the fixed catalyst bed in long-term operation is firstly held for as long as possible in temperature zone A, and simultaneously at comparatively low absolute values. The latter is the case in the inventive long-term mode of operation.

Of course, the inventive procedure can also be employed successfully in the case of propene velocities on the fixed catalyst bed of <140 l (STP)/l·h, or $\leq 130$ l (STP)/l·h, or $\leq 120$ l (STP)/l·h, or $\leq 110$ l (STP)/l·h, or $\leq 100$ l (STP)/l·h, or $\leq 90$ l (STP)/l·h, or $\leq 80$ l (STP)/l·h (but generally $\geq 60$ l (STP)/l·h). With an increasing decrease in propene velocity on the fixed catalyst bed, however, the procedure according to WO 2007/082827 becomes more advantageous compared to such a procedure.

The inventive procedure can likewise also be applied analogously to a heterogeneously catalyzed partial gas phase oxidation of acrolein to acrylic acid. Due to the comparatively lower exothermicity of this partial oxidation and a higher thermal sensitivity of the total oxidation (full combustion) of acrylic acid compared to acrolein, however, a procedure according to WO 2007/082827 is preferable in this case at high acrolein velocities on the fixed catalyst bed.

On completion of fresh charging of the fixed catalyst bed or on completion of regeneration of the fixed catalyst bed (for example by conducting a hot gas mixture of molecular oxygen and inert gas through the fixed catalyst bed, as described in the prior art cited in this regard in this document), the process according to the invention normally cannot be accommodated directly at the high target propene velocity on the fixed catalyst bed for steady-state operation, including the accompanying target conversion of propene based on a single pass of the reaction gas mixture through the fixed catalyst bed.

This is because the freshly prepared or freshly regenerated catalysts comprising oxidic active materials are present in a kind of hyperactive (oxygen over-supplied) state which would lead within a short time especially to extreme values for $T^{maxA}$ in the case of direct application of the steady-state operating conditions.

This fact is normally counteracted in practice by performing the heterogeneously catalyzed partial oxidation process, in the event of such a startup or restart, initially at comparatively lower values for the propene velocity on the fixed catalyst bed and/or the propene conversion based on a single pass of the reaction gas mixture through the fixed catalyst bed (appropriately in application terms, $\Delta T^{BA}$ is also kept at >0° C.). Subsequently, these startup or restart conditions are advantageously changed to the operating conditions of the desired steady-state operation in such a way that $T^{maxA}$ is always $>T^{maxB}$ and that at no time is $T^{maxA} > T^{maxA}$ in the steady operating state +3° C. (in other words, the $T^{maxA}$ value for the steady operating state is exceeded by at most 3° C. on the route to the steady operating state). Advantageously, $T^{maxA}$ in the process according to the invention will not exceed 425° C. or better 420° C., or even better 410° C. Typically, $T^{maxA}$ in the process according to the invention will, however, be ≥350° C., usually ≥360° C. and often ≥370° C. or ≥380° C.

The operating phases of the heterogeneously catalyzed gas phase partial oxidation process from startup or restart of the fixed catalyst bed until attainment of the conditions of steady-state operation (until attainment of steady-state operation) are not attributed to the process according to the invention for long-term operation (they generally extend to ≤72 h, frequently ≤48 h or ≤24 h).

Preferably in accordance with the invention, the inventive procedure will be employed in combination with an intermediate regeneration according to the teaching of DE-A 10351269, WO 2004/085369, DE-A 10350812 or EP-A 614872.

In addition, before the fixed catalyst bed is fully exchanged, a partial bed exchange can be undertaken according to the teaching of DE-A 10232748 or of WO 2004/009525. In all cases, this partial fixed catalyst bed exchange may extend, in flow direction of the reaction gas mixture, to up to 80%, or only up to 70%, or only to up to 60%, or only to up to 50%, or only to up to 40%, or only to up to 30%, or preferably to up to 25%, more preferably to 30 to 50% and most preferably to 35 to 45% of the bed length of the particular fixed catalyst bed (an outer charge consisting of 100% inert material (the first charge from the flow point of view) is, as also for the other purposes of this document, not considered to form part of the fixed catalyst bed; correspondingly, for the purposes of the present invention, a final charge consisting of 100% inert material (the end charge from the flow point of view) is normally (unless explicitly stated otherwise) not considered to form part of the fixed catalyst bed; an intermediate charge consisting of 100% inert material (unless explicitly stated otherwise) in this document is, however, typically considered to form part of the fixed catalyst bed).

Appropriately, the aforementioned percentage for a partial catalyst exchange is frequently not less than 5%, or not less than 10%, or not less than 20%.

The molar ratio of $O_2:C_3H_6$ in the reaction gas input mixture for an inventive partial oxidation of propene to acrolein is, in accordance with the invention, ≥1. Typically, this ratio will be at values of ≤3. Frequently, the molar ratio of $O_2:C_3H_6$ in the reaction gas input mixture in the process according to the invention is ≥1.2, or ≥1.5 and ≤2.0.

Generally, it is favorable for an inventive heterogeneously catalyzed partial oxidation of propene to acrolein when the product gas mixture still comprises (for example up to 3% by volume of) unconverted molecular oxygen.

Useful fresh (not used beforehand, as yet unused) catalysts for the fixed catalyst bed (the fixed bed catalyst charge) of an inventive gas phase partial oxidation of propene to acrolein include all of those whose active material is at least one multimetal oxide comprising Mo, Bi and Fe.

Catalysts advantageous in accordance with the invention are those whose active material is a multimetal oxide which comprises at least the elements Mo, Fe and Bi, and additionally at least one of the two elements Ni and Co. It is found to be favorable when, of the five elements (other than oxygen) mentioned above, based on the total molar amount G thereof present in the active material, the element Mo accounts for the greatest molar proportion (in mol % based on the total molar amount G).

Multielement oxide active materials particularly suitable in accordance with the invention are thus especially those of the general formula I of DE-A 19955176, the multielement oxide active materials of the general formula I of DE-A 19948523, the multielement oxide active materials of the general formulae I, II and III of DE-A 10101695, the multielement oxide active materials of the general formulae I, II and III of DE-A 19948248 and the multielement oxide active materials of the general formulae I, II and III of DE-A 19955168, and also the multielement oxide active materials specified in documents EP-A 700 714, DE-A 102009047291, DE-A 102007005606, DE-A 10200840094, WO 2008/087116, WO 2008/087115, WO 2007/017431, DE-A 10 2007 004961, DE-A-10 2008 040093, DE application 102008042064.6, DE application 102008042061.1 and DE-A 102008042060. This is especially true of the exemplary embodiments disclosed in the latter five documents. Equally suitable as multielement oxide active materials for the process according to the invention are those which are recommended in WO 2007/082827 and in WO 2005/042459 for the heterogeneously catalyzed partial gas phase partial oxidation.

Additionally suitable for the fresh fixed bed catalyst charge of an inventive propene partial oxidation are the multimetal oxide catalysts which comprise Mo, Bi and Fe and are disclosed in the documents research disclosure No. 497012 dated Aug. 29, 2005, DE-A 100 46 957, DE-A 100 63 162, DE-C 33 38 380, DE-A 199 02 562, EP-A 15 565, DE-C 23 80 765, EP-A 807 465, EP-A 279 374, DE-A 33 00 044, EP-A 575 897, U.S. Pat. No. 4,438,217, DE-A 198 55 913, WO 98/24746, DE-A 197 46 210 (those of the general formula II), JP-A 91/294239 and EP-A 293 224. This is especially true of the exemplary embodiments (including the comparative examples) in these documents, among which those of research disclosure No. 497012, of EP-A 15 565, of EP-A 575 897, of DE-A 197 46 210 and of DE-A 198 55 913 are particularly preferred. Particular emphasis should be given in this context to a catalyst according to example 1c from EP-A 15 565, and a catalyst which is to be prepared in a corresponding manner but whose active material has the composition $Mo_{12}Ni_{6.5}Zn_2Fe_2Bi_1P_{0.0065}K_{0.06}Ox \cdot 10\ SiO_2$. Emphasis should additionally be given to the example with the serial No. 3 from DE-A 198 55 913 (stoichiometry: $Mo_{12}Co_7Fe_3Bi_{0.6}K_{0.08}Si_{1.6}Ox$) as an unsupported hollow cylindrical catalyst of geometry 5 mm×3 mm×2 mm or 5 mm×2 mm×2 mm (in each case external diameter×height× internal diameter), and to the unsupported multimetal oxide II catalyst according to example 1 of DE-A 197 46 210. The multimetal oxide catalysts of U.S. Pat. No. 4,438,217 should additionally be mentioned. The latter is especially true when they have a hollow cylindrical geometry of dimensions 5.5 mm×3 mm×3.5 mm, or 5 mm×2 mm×2 mm, or 5 mm×3 mm×2 mm, or 6 mm×3 mm×3 mm, or 7 mm×3 mm×4 mm (in each case external diameter×height×internal diameter). Equally suitable are the multimetal oxide catalysts and geometries of DE-A 101 01 695 or WO 02/062737.

Additionally suitable are example 1 from DE-A 100 46 957 (stoichiometry: $[Bi_2W_2O_9 \times 2WO_3]_{0.5} \cdot [Mo_{12}Co_{5.6}Fe_{2.94}Si_{1.59}K_{0.08}O_x]_1$) as an unsupported hollow cylindrical (ring) catalyst of geometry 5 mm×3 mm×2 mm or 5 mm×2 mm×2 mm (in each case external diameter×length× internal diameter), and eggshell catalysts 1, 2 and 3 from DE-A 100 63 162 (stoichiometry: $Mo_{12}Bi_{1.0}Fe_3Co_7Si_{1.6}K_{0.08}$), except as annular eggshell catalysts of corresponding eggshell thickness and applied to support rings of geometry 5 mm×3 mm×1.5 mm or 7 mm×3 mm×1.5 mm (in each case external diameter×length×internal diameter).

A multitude of the multielement oxide active materials suitable for the process according to the invention can be encompassed by the general formula I $$Mo_{12}Bi_aFe_bX^1_cX^2_dX^3_eX^4_fO_n \quad (I)$$

in which the variables are each defined as follows:
$X^1$=nickel and/or cobalt,
$X^2$=thallium, an alkali metal and/or an alkaline earth metal,
$X^3$=zinc, phosphorus, arsenic, boron, antimony, tin, cerium, lead and/or tungsten,
$X^4$=silicon, aluminum, titanium and/or zirconium,
a=0.05 to 5,
b=0.01 to 5, preferably 2 to 4,
c=0.1 to 10, preferably 3 to 10,
d=0 to 2, preferably 0.02 to 2,
e=0 to 8, preferably 0 to 5,
f=0 to 10 and
n=a number which is determined by the valency and frequency of the elements in I other than oxygen.

They are obtainable in a manner known per se (see, for example, DE-A 40 23 239) and are typically used shaped in substance to spheres, rings or cylinders, or else in the form of eggshell catalysts, i.e. preshaped inert support bodies coated with the active material. It will be appreciated, however, that they may also be employed in powder form as catalysts.

In principle, active materials of the general formula I can be prepared in a simple manner by obtaining, from suitable sources of the elemental constituents thereof, a very intimate, preferably finely divided, dry mixture whose composition corresponds to the stoichiometry thereof, and calcining it at temperatures of 350 to 650° C. The calcination can be effected either under inert gas or under an oxidative atmosphere, for example air (mixture of inert gas and oxygen), or else under a reducing atmosphere (for example mixture of inert gas, $NH_3$, CO and/or $H_2$). The calcination time may be a few minutes to a few hours and typically decreases with temperature. Useful sources for the elemental constituents of the multimetal oxide active materials I include those compounds which are already oxides and/or those compounds which can be converted to oxides by heating, at least in the presence of oxygen.

In addition to the oxides, useful such starting compounds are in particular halides, nitrates, formates, oxalates, citrates, acetates, carbonates, amine complexes, ammonium salts and/or hydroxides (compounds such as $NH_4OH$, $(NH_4)_2CO_3$, $NH_4NO_3$, $NH_4CHO_2$, $CH_3COOH$, $NH_4CH_3CO_2$ and/or ammonium oxalate, which decompose and/or can be broken down to compounds which escape in gaseous form no later than in the course of the later calcining, can additionally be incorporated into the intimate dry mixture).

The intimate mixing of the starting compounds to prepare multimetal oxide active materials I can be effected in dry or wet form. When it is effected in dry form, the starting compounds are appropriately used in the form of fine powder and, after the mixing and optional compaction, subjected to calcination. Preference is given, however, to intimate mixing in wet form. This typically involves mixing the starting compounds with one another in the form of an aqueous solution and/or suspension. Particularly intimate dry mixtures are obtained in the mixing process described when the starting materials are exclusively sources of the elemental constituents present in dissolved form. The solvent used is preferably water. Subsequently, the resulting aqueous material is dried, the drying operation preferably being effected by spray-drying the aqueous mixture with exit temperatures of 100 to 150° C.

Typically, the multimetal oxide active materials of the general formula I are used in the (fresh) fixed bed catalyst charge for an inventive gas phase partial oxidation to acrolein not in powder form but shaped to particular catalyst geometries, in which case the shaping may precede or follow the final calcination. For example, the powder form of the active material or the uncalcined and/or partially calcined precursor material thereof can be used to produce unsupported catalysts by compacting to the desired catalyst geometry (for example by tableting or extruding), in which case it is optionally possible to add assistants, for example graphite or stearic acid as lubricants and/or shaping assistants, and reinforcing agents such as microfibers of glass, asbestos, silicon carbide or potassium titanate. Suitable unsupported catalyst geometries are, for example, solid cylinders or hollow cylinders with an external diameter and a length of 2 to 10 mm. In the case of the hollow cylinders, a wall thickness of 1 to 3 mm is appropriate. It will be appreciated that the unsupported catalyst may also have spherical geometry, in which case the sphere diameter may be 2 to 10 mm.

A particularly favorable hollow cylinder geometry is 5 mm×3 mm×2 mm (external diameter×length×internal diameter), especially in the case of unsupported catalysts.

It will be appreciated that the pulverulent active material or the pulverulent precursor material thereof, which is yet to be calcined and/or has been partially calcined, can also be shaped by application to preshaped inert catalyst supports. The coating of the support bodies to produce eggshell catalysts is generally performed in a suitable rotatable vessel, as known, for example, from DE-A 29 09 671, EP-A 293 859 or from EP-A 714 700. Appropriately, the support bodies are coated by moistening the powder material to be applied and drying it again after the application, for example by means of hot air. The layer thickness of the powder material applied to the support body is appropriately selected within the range of 10 to 1000 μm, preferably in the range of 50 to 500 μm and more preferably in the range of 150 to 250 μm.

The support materials used may be customary porous or nonporous aluminum oxides, silicon dioxide, thorium dioxide, zirconium dioxide, silicon carbide, or silicates such as magnesium or aluminum silicate. They generally behave essentially inertly with regard to the inventive target reaction. The support bodies may have a regular or irregular shape, preference being given to regular-shaped support bodies with distinct surface roughness, for example spheres or hollow cylinders. It is suitable to use essentially nonporous, spherical steatite supports with a rough surface (for example C 220 steatite from CeramTec), the diameter of which is 1 to 8 mm, preferably 4 to 5 mm. However, it is also suitable to use cylinders as support bodies, the length of which is 2 to 10 mm and the external diameter of which is 4 to 10 mm. In the case of rings suitable in accordance with the invention as support bodies, the wall thickness is additionally typically 1 to 4 mm. Annular support bodies for use with preference in accordance with the invention have a length of 2 to 6 mm, an external diameter of 4 to 8 mm and a wall thickness of 1 to 2 mm. Support bodies suitable in accordance with the invention are in particular also rings of geometry 7 mm×3 mm×4 mm (external diameter×length×internal diameter). The fineness of the catalytically active oxide materials to be applied to the surface of the support body is of course adjusted to the desired shell thickness (cf. EP-A 714 700).

Multimetal oxide active materials suitable for the (fresh) catalysts of an inventive partial oxidation for preparation of acrolein are additionally materials of the general formula II, $$[Y^1_{a'}Y^2_{b'}O_{x'}]_p[Y^3_{c'}Y^4_{d'}Y^5_{e'}Y^6_{f'}Y^7_{g'}Y^8_{h'}O_{y'}]_q \quad (II)$$

in which the variables are each defined as follows:
$Y^1$=only bismuth or bismuth and at least one of the elements tellurium, antimony, tin and copper,
$Y^2$=molybdenum, or tungsten, or molybdenum and tungsten,
$Y^3$=an alkali metal, thallium and/or samarium, $Y^4$=nickel and/or cobalt, and optionally one or more of the elements copper, manganese, zinc, tin, cadmium, mercury and the alkaline earth metals,
$Y^5$=iron or iron and at least one of the elements chromium and cerium,
$Y^6$=phosphorus, arsenic, boron and/or antimony,
$Y^7$=a rare earth metal, titanium, zirconium, niobium, tantalum, rhenium, ruthenium, rhodium, silver, gold, aluminum, gallium, indium, silicon, germanium, lead, thorium and/or uranium,
$Y^8$=molybdenum, or molybdenum and tungsten,
a'=0.01 to 8,
b'=0.1 to 30,
c'=0 to 4,
d'=0.1 to 20,
e'>0 to 20, preferably 0.01 or 0.1 to 20,
f'=0 to 6,
g'=0 to 15,
h'=8 to 16,
x', y'=numbers which are determined by the valency and frequency of the elements in II other than oxygen, and
p, q=numbers whose p/q ratio is 0.1 to 10,
comprising three-dimensional regions which are delimited from their local environment owing to their different composition than their local environment and which are of the chemical composition $Y^1{}_a Y^2{}_b O_{x'}$ and whose greatest diameter (longest line which goes through the center of the region and connects two points on the surface (interface) of the region) is 1 nm to 100 μm, frequently 10 nm to 500 nm or 1 μm to 50 or to 25 μm.

Particularly advantageous inventive multimetal oxide materials II are those in which $Y^1$ is only bismuth.

Among these, preference is given in turn to those which are of the general formula III,

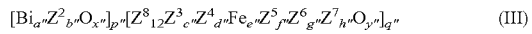

$$[Bi_{a''}Z^2{}_{b''}O_{x''}]_{p''}[Z^8{}_{12}Z^3{}_{c''}Z^4{}_{d''}Fe_{e''}Z^5{}_{f''}Z^6{}_{g''}Z^7{}_{h''}O_{y''}]_{q''} \quad (III)$$

in which the variants are each defined as follows:
$Z^2$=molybdenum, or tungsten, or molybdenum and tungsten,
$Z^3$=nickel and/or cobalt,
$Z^4$=thallium, an alkali metal and/or an alkaline earth metal,
$Z^5$=phosphorus, arsenic, boron, antimony, tin, cerium and/or lead,
$Z^6$=silicon, aluminum, titanium and/or zirconium,
$Z^7$=copper, silver and/or gold,
$Z^8$=molybdenum, or molybdenum and tungsten,
a''=0.1 to 1,
b''=0.2 to 2,
c''=3 to 10,
d''=0.02 to 2,
e''=0.01 to 5, preferably 0.1 to 3,
f''=0 to 5,
g''=0 to 10,
h''=0 to 1,
x'', y''=numbers which are determined by the valency and frequency of the elements in III other than oxygen,
p'', q''=numbers whose p''/q'' ratio is 0.1 to 5, preferably 0.5 to 2, very particular preference being given to those materials III in which $Z^2{}_{b''}$=(tungsten)$_{b''}$ and $Z^8{}_{12}$=(molybdenum)$_{12}$.

It is additionally advantageous when at least 25 mol % (preferably at least 50 mol % and more preferably at least 100 mol %) of the total proportion of $[Y^1{}_a Y^2{}_b O_x]_p$ ($[Bi_{a''}Z^2{}_{b''}O_{x''}]_{p''}$) of the multimetal oxide materials II (multimetal oxide materials III) suitable in accordance with the invention are present in the multimetal oxide materials II (multimetal oxide materials III) suitable in accordance with the invention in the form of three-dimensional regions which are delimited from their local environment owing to their different chemical composition than their local environment and are of the chemical composition $Y^1{}_a Y^2{}_b O_{x'}$ [$Bi_{a''}Z^2{}_{b''}O_{x''}$] and whose greatest diameter is in the range of 1 nm to 100 μm.

With regard to the shaping, the statements made for the multimetal oxide material I catalysts apply with regard to multimetal oxide material II catalysts.

The preparation of multimetal oxide material II active materials is described, for example, in DE application 102008054586.4, DE-A 102008040093, DE-A 102008040094, EP-A 575 897 and in DE-A 198 55 913.

The inert support materials recommended above are also options, inter alia, as inert materials for dilution and/or delimitation of the appropriate fixed catalyst bed, or as the protective preliminary bed thereof or as a downstream bed.

In principle, the volume-specific activity of the (fresh) fixed catalyst bed in flow direction of the reaction gas mixture in an inventive partial oxidation of propene to acrolein may be constant over the length of the flow path (i.e. over the length of the fixed catalyst bed), or advantageously increase at least once (continuously or abruptly or in stages). It is advantageous when the active material composition does not change over the length of the flow path of the reaction gas mixture (i.e. within the fresh fixed catalyst bed).

It is advantageous in accordance with the invention when the fixed bed catalyst charge consists of at least two spatially successive fixed bed catalyst charge zones, the volume-specific activity within one fixed bed catalyst charge zone being substantially constant and increasing sharply at the transition from one fixed bed catalyst charge zone into another fixed bed catalyst charge zone in flow direction of the reaction gas mixture.

The volume-specific (i.e. normalized to the unit of the particular bed volume) activity of a fixed bed catalyst charge zone can then be adjusted over the fixed bed catalyst charge zone in a substantially constant manner by starting from a basic amount of shaped catalyst bodies prepared in a uniform manner (their bed corresponds to the maximum achievable volume-specific activity) and homogeneously diluting it in the particular fixed bed catalyst charge zone with shaped bodies (shaped diluent bodies) which behave substantially inertly with regard to the heterogeneously catalyzed partial gas phase oxidation. The higher the proportion of shaped diluent bodies selected, the smaller the amount of active material and catalyst activity present in a certain volume of the bed. Useful materials for such inert shaped diluent bodies are in principle all of those which are suitable as support material for eggshell catalysts suitable in accordance with the invention.

Useful materials of this kind include, for example, porous or nonporous aluminum oxides, silicon dioxide, thorium dioxide, zirconium dioxide, silicon carbide, silicates such as magnesium silicate or aluminum silicate or the steatite already mentioned (e.g. C 220 steatite from CeramTec).

The geometry of such inert shaped diluent bodies may in principle be as desired. In other words, they may, for example, be spheres, polygons, solid cylinders or else rings. According to the invention, the inert shaped diluent bodies selected will preferably be those whose geometry corresponds to that of the shaped catalyst bodies to be diluted with them.

It is favorable in accordance with the invention, as already stated, when the chemical composition of the active material used does not vary over the entire fixed bed catalyst charge. In other words, although the active material used for a single shaped catalyst body can be a mixture of different multimetal oxides comprising the elements Mo, Fe and Bi, the same mixture then has to be used for all shaped catalyst bodies of the fixed bed catalyst charge.

A volume-specific activity increasing zone by zone (which is particularly advantageous) over the fixed bed catalyst charge in flow direction of the reaction gas mixture can therefore be achieved in a simple manner, for example, by beginning the bed in a first fixed bed catalyst charge zone with a high proportion of inert shaped diluent bodies based on one type of shaped catalyst bodies, and then reducing this proportion of shaped diluent bodies zone by zone in flow direction.

However, such a zone by zone increase in the volume-specific activity advantageous in accordance with the invention is also possible, for example, by increasing the thickness of the active material layer applied to the support zone by zone at constant geometry and active material type of a coated shaped catalyst body or, in a mixture of eggshell catalysts having the same geometry but having different proportions by weight of the active material by increasing the proportion of shaped catalyst bodies having higher active material content zone by zone. Alternatively, the active materials themselves can be diluted in the course of the active material preparation by, for example, incorporating inert, diluting materials such as hard-fired silica into the dry mixture of starting compounds to be calcined. Different amounts of diluting material added lead automatically to different activities. The more diluting material is added, the lower the resulting activity will be. A similar effect can also be achieved, for example, in the case of mixtures of unsupported catalysts and of eggshell catalysts (having identical active material) by varying the mixing ratio in an appropriate manner. A variation in the volume-specific activity can also be achieved by the use of catalyst geometries having different bulk density (for example, in the case of unsupported catalysts having identical active material composition of the different geometries). It is of course also possible to use the variants described in combination.

It is of course also possible to use mixtures of catalysts having chemically different active material composition and, as a consequence of this different composition, having different activity for the fixed bed catalyst charge. These mixtures may in turn, zone by zone, be varied in their composition and/or be diluted with different amounts of inert shaped diluent bodies so that the volume-specific activity in flow direction of the reaction gas mixture increases zone by zone.

Upstream and/or downstream of the fixed bed catalyst charge may be disposed beds consisting exclusively of inert material (for example only shaped diluent bodies) (in this document, they are not included for terminology purposes in the fixed bed catalyst charge, since they do not comprise any shaped bodies which have multimetal oxide active material). The shaped diluent bodies used for the inert bed may have the same geometry as the shaped catalyst bodies used in the fixed bed catalyst charge. However, the geometry of the shaped diluent bodies used for the inert bed may also be different to the abovementioned geometry of the shaped catalyst bodies (for example, spherical instead of annular).

Frequently, the shaped bodies used for such inert beds have the annular geometry 7 mm×7 mm×4 mm or 7 mm×3 mm×4 mm (in each case external diameter×length×internal diameter) or the spherical geometry having the diameter d=4-5 mm. Temperature zones A and B in the process according to the invention may also extend to the inert beds. According to the invention, it is advantageous when neither temperature zone A nor temperature zone B for an inventive partial oxidation of propene to acrolein covers more than three fixed bed catalyst charge zones (according to the invention, at least one fixed bed catalyst charge zone is advantageously covered by both temperature zones).

According to the invention, it is particularly preferred when the entire fixed bed catalyst charge comprises not more than five, appropriately not more than four or three, fixed bed catalyst charge zones.

According to the invention, at the transition from one fixed bed catalyst charge zone to another fixed bed catalyst charge zone (in flow direction of the reaction gas mixture) of the fixed bed catalyst charge, the volume-specific active material (i.e. the weight of the multimetal oxide active material present in the uniform bed volume) should (in the case of uniform active material over the entire fixed bed catalyst charge) appropriately increase by at least 5% by weight, preferably by at least 10% by weight (this applies in particular in the case of uniform shaped catalyst bodies over the entire fixed bed catalyst charge). In general, this increase in the process according to the invention for heterogeneously catalyzed partial oxidation of propene to acrolein will not be more than 50% by weight, usually not more than 40% by weight. According to the invention, in the case of uniform active material over the entire fixed bed catalyst charge, the difference in the volume-specific active material of the fixed bed catalyst charge zone having the lowest volume-specific activity and the fixed bed catalyst charge zone having the highest volume-specific activity should advantageously also not be more than 50% by weight, preferably not more than 40% by weight, and generally not more than 30% by weight.

In a process according to the invention for heterogeneously catalyzed partial oxidation of propene to acrolein, the fixed bed catalyst charge will frequently consist of only two fixed bed catalyst charge zones.

Preferably in accordance with the invention, the last fixed bed catalyst charge zone of the fixed bed catalyst charge in flow direction of the reaction gas mixture is undiluted. In other words, it preferably consists exclusively of shaped catalyst bodies. If required, it may also consist of a bed of shaped catalyst bodies whose volume-specific activity is reduced, for example by dilution with inert material, for example by 10%.

When the fixed bed catalyst charge for a heterogeneously catalyzed partial oxidation of propene to acrolein consists of only two fixed bed catalyst charge zones, it is generally advantageous in accordance with the invention when the fixed bed catalyst charge zone having the highest volume-specific activity does not project into temperature zone A (especially when the heating in temperature zone A and temperature zone B is effected by means of a flowing heat carrier which in each case flows in countercurrent to the reaction gas mixture (viewed over the reactor)). In other words, the fixed bed catalyst charge zone having the lower volume-specific activity will favorably project into temperature zone B and the fixed bed catalyst charge zone having the higher volume-specific activity will begin and end in temperature zone B (i.e. have its beginning beyond the transition from temperature zone A to temperature zone B).

Especially in the case of additional use of, based on the reaction gas input mixture, for example, up to 50% by volume of propane as an inert diluent gas, it has, however, been found to be appropriate to allow the fixed bed catalyst charge zone with the highest volume-specific activity to project into temperature zone A. This is especially true in the case of countercurrent mode (viewed over the reactor) of salt baths and reaction gas mixture.

When the fixed bed catalyst charge consists only of three fixed bed catalyst charge zones, it is generally equally advantageous in accordance with invention when the fixed bed catalyst charge zone having the higher volume-specific activity does not project into temperature zone A but begins and ends in temperature zone B, i.e. has its beginning beyond the transition from temperature zone A to temperature zone B (especially when the heating in temperature zone A and in temperature zone B is effected by means of a flowing heat carrier which in each case flows in countercurrent to the reaction gas mixture). In other words, the fixed bed catalyst charge zone having the second highest volume-specific activity in this case will normally project into both temperature zone A and temperature zone B.

When the fixed bed catalyst charge consists of four fixed bed catalyst charge zones, it is generally advantageous in accordance with the invention when the fixed bed catalyst charge zone having the third highest volume-specific activity projects into both temperature zone A and into temperature zone B (especially when the heating in temperature zone A and in temperature zone B is effected by means of a flowing heat carrier which in each case flows in countercurrent to the reaction gas mixture).

In the case of cocurrent flow of the reaction gas mixture and heat carriers in temperature zones A and B, it may be advantageous in the process according to the invention when the fixed bed catalyst charge zone having the highest volume-specific activity within the fixed bed catalyst charge projects into temperature zone A.

Generally, the volume-specific activity between two fixed bed catalyst charge zones of a fixed bed catalyst charge can be differentiated experimentally in a simple manner by passing the same reaction gas mixture comprising propene, under identical boundary conditions (preferably the conditions of the contemplated process), over fixed bed catalyst charges of the same length, but in each case each according to the composition of the particular fixed bed catalyst charge zone. The higher amount of propene converted indicates the higher volume-specific activity.

When the total length of the fixed bed catalyst charge is L, it is advantageous in accordance with the invention if there is no transition from one fixed bed catalyst charge zone to another fixed bed catalyst charge zone within the region of $$X \pm L\frac{4}{100}$$

or within the region of $$X \pm L\frac{3}{100}$$

or within the region of $$X \pm L\frac{2}{100},$$

where X is the location (the position) within the fixed bed catalyst charge of the transition from temperature zone A to temperature zone B.

Preferably in accordance with the invention, the fixed bed catalyst charge (not including mere inert upstream and/or downstream beds) in the process according to the invention is structured as follows in flow direction of the reaction gas mixture.

First, to a length of 10 to 60%, preferably 20 to 55%, more preferably 30 to 55% and most preferably 40 to 50% (i.e., for example, to a length of 0.90 to 1.70 m, preferably 1.10 to 1.60 m), each of the total length of the fixed bed catalyst charge, a homogeneous mixture of shaped catalyst bodies and shaped diluent bodies (both preferably having substantially the same geometry), in which the proportion by weight of the shaped diluent bodies (the densities of shaped catalyst bodies and of shaped diluent bodies generally differ only slightly) is normally 5 to 40% by weight, or 10 to 40% by weight, or 20 to 40% by weight, or 25 to 35% by weight. According to the invention, this first zone of the fixed bed catalyst charge is advantageously followed up to the end of the length of the fixed bed catalyst charge (i.e., for example, to a length of 1.00 (or 1.40 m) to 3.00 m, preferably 1.00 to 2.50 or to 2.00 m) either by a bed of shaped catalyst bodies diluted only to a slighter extent (than in the first zone), or, most preferably, an unaccompanied (undiluted) bed of the same shaped catalyst bodies which have also been used in the first zone. The aforesaid applies especially when the shaped catalyst bodies used in the fixed bed catalyst charge are unsupported catalyst rings or eggshell catalyst rings (in particular those which are specified as preferred in this document). For the purposes of the abovementioned structuring, both the shaped catalyst bodies and the shaped diluent bodies in the process according to the invention advantageously have substantially the ring geometry 5 mm×3 mm×2 mm (external diameter×length×internal diameter).

The aforementioned also applies when, instead of inert shaped diluent bodies, shaped eggshell catalyst bodies are used whose active material content is 2 to 15% by weight lower than the active material content of any shaped eggshell catalyst bodies used at the end of the fixed bed catalyst charge.

A pure inert material bed whose length, based on the length of the fixed bed catalyst charge, is appropriately 5 to 20% generally leads to the fixed bed catalyst charge in flow direction of the reaction gas mixture. It is normally utilized as a heating zone for the reaction gas mixture.

According to the invention, the fixed bed catalyst charge zone having the lower volume-specific activity in the aforementioned fixed bed catalyst charges then advantageously extends into temperature zone B for 5 to 20%, frequently 5 to 15%, of its length.

Appropriately in accordance with the invention, temperature zone A also extends to a preliminary bed of inert material which is optionally used for the fixed bed catalyst charge.

It will be appreciated that temperature zones A, B in the process according to the invention may be followed by further additional temperature zones. However, this is not preferred in accordance with the invention.

For eggshell catalysts of the fixed bed catalyst charge, especially suitable support bodies are those which have an increased surface roughness, since they generally cause increased adhesive strength of the coating of active material applied.

The surface roughness $R_z$ of the support body is preferably in the range from 30 to 200 μm, preferably 30 to 100 μm (determined to DIN 4768 sheet 1 with a Hommel tester for DIN-ISO surface measurements from Hommelwerke). The aforementioned is especially true for support bodies of C 220 steatite from CeramTec. In principle, the support materials may be porous or nonporous.

In an appropriate manner in terms of application, a process according to the invention for partial oxidation of propene to acrolein is carried out in a two-zone tube bundle reactor, as described, for example, in DE-As 19910508, 19948523, 19910506 and 19948241. A preferred variant of a two-zone tube bundle reactor which can be used in accordance with the invention is disclosed by DE-C 2830765. However, the two-zone tube bundle reactors disclosed in DE-C 2513405, U.S. Pat. No. 3,147,084, DE-A 2201528, EP-A 383224, WO 2007/082827, WO 2004/08362 WO 2004/085362, EP-A1547994 and DE-A 2903218 are also suitable for carrying out such a process.

In other words, in the simplest manner, the fixed bed catalyst charge to be used in accordance with the invention for such a process (possibly with downstream and/or upstream inert beds) is disposed in the metal tubes of a tube bundle reactor and two substantially spatially separated heating media, generally salt melts, are conducted around the metal tubes. The tube section over which the particular salt bath extends represents a temperature zone in accordance with the invention. In other words, in the simplest manner, for example, a salt bath A flows around that section of the tubes (temperature zone A) in which the oxidative conversion of propene (in single pass) proceeds until a conversion $C^A$ in the range required in accordance with the invention is achieved, and a salt bath B flows around the section of the tubes (temperature zone B) in which the subsequent oxidative conversion of propene (in single pass) proceeds until a conversion value $C^B$ of at least 90 mol % is achieved (if required, the temperature zones A, B to be used in accordance with the invention may be followed by further temperature zones which are maintained at individual temperatures).

Appropriately in terms of application, an inventive propene partial oxidation to acrolein does not comprise any further temperature zones. In other words, salt bath B appropriately flows around the section of the tubes in which the subsequent oxidative conversion of propene (in single pass) proceeds up to a conversion value of ≥90 mol %, or ≥92 mol % or ≥94 mol % or more.

According to the invention, both salt baths A, B can be conducted in cocurrent or in countercurrent through the space surrounding the reaction tubes relative to flow direction of the reaction gas mixture flowing through the reaction tubes. It is of course also possible in accordance with the invention to employ cocurrent flow in temperature zone A and countercurrent flow in temperature zone B (or vice versa).

In all of the aforementioned cases, it is of course possible to superimpose a transverse flow on the parallel flow of the salt melt, relative to the reaction tubes, taking place within the particular temperature zone, so that the individual reaction zone corresponds to a tube bundle reactor as described in EP-A 700 714, or in EP-A 700 893, or in EP-A 1547944, which results overall in a meandering flow profile of the heat exchange medium in a longitudinal section through the catalyst tube bundle.

The flow rate of the fluid heat carrier is, according to the teaching of the aforementioned documents, advantageously such that, in the event of a further increase in this flow rate, essentially no increase in the heat transfer from the reaction tube interior to the heat carrier is brought about.

In other words, typical heat transfer coefficients from the material shell of the reaction space (for example of the outer wall of the reaction tube) to the fluid heat carrier (for example to the salt melt) are, in the process according to the invention, advantageously ≥700 W/m²·K, particularly advantageously ≥1000 W/m²·K, very particularly advantageously ≥1500 or ≥2000 W/m²·K, but generally ≤3000 W/m²·K.

Appropriately, a reaction gas input mixture is fed to the fixed bed catalyst charge preheated to the temperature of temperature zone A.

Typically, the catalyst tubes in the two-zone tube bundle reactors are manufactured from ferritic steel and typically have a wall thickness of 1 to 3 mm. Their internal diameter is generally 20 to 30 mm, frequently 21 to 26 mm. Their length is appropriately 2 to 4 m, preferably 2.5 to 3.5 m. In each temperature zone, the fixed bed catalyst charge occupies at least 60%, or at least 75%, or at least 90%, of the length of the zone. Any remaining length is optionally occupied by an inert bed. It is advantageous in terms of application for the number of catalyst tubes accommodated in the tube bundle vessel to be at least 5000, preferably at least 10000. Frequently, the number of catalyst tubes accommodated in the reaction vessel is 15000 to 30000 or to 40000. Tube bundle reactors having a number of catalyst tubes above 50000 are usually exceptional. Within the vessel, the catalyst tubes are normally homogeneously distributed (preferably 6 equidistant adjacent tubes per catalyst tube), and the distribution is appropriately selected in such a way that the separation of the central internal axes of immediately adjacent catalyst tubes (known as the catalyst tube pitch) is 35 to 45 mm (cf., for example, EP-B 468 290).

Suitable heat exchange media for the two-zone method are also in particular fluid heating media. It is particularly favorable to use melts of salts such as potassium nitrate, potassium nitrite, sodium nitrite and/or sodium nitrate, or of low-melting metals such as sodium, mercury and also alloys of different metals.

In general, in all of the aforementioned flow arrangements in the two-zone tube bundle reactors, the flow rate of the heat exchange medium within the two heat exchange medium circuits required is such that the temperature of the heat exchange medium rises from the entrance into the temperature zone to the exit from the temperature zone (as a result of the exothermicity of the reaction) by 0 to 15° C. In other words, the aforementioned ΔT may, in accordance with the invention, be 1 to 10° C., or 2 to 8° C., or 3 to 6° C. Preferably in accordance with the invention, it is low.

The entrance temperatures of the heat exchange media into temperature zones A, B of the two-zone tube bundle reactors in a propene partial oxidation to acrolein are to be selected in accordance with the invention such that they correspond to the temperatures and temperature differences $\Delta T^{BA}$ required for temperature zones A, B in this document for this reaction. In inventive long-term operation, they are to be changed in accordance with the invention.

It should be pointed out once again here that, for the performance of an inventive propene partial oxidation to acrolein, it is also possible in particular to use the two-zone tube bundle reactor type which is described in DE-B 2201528 and includes the possibility of removing a portion of the hot heat exchange medium of temperature zone B to temperature zone A, in order optionally to heat a cold reaction gas input mixture or a cold cycle gas. The tube bundle characteristics within an individual temperature zone may also be configured as described in EP-A 382098.

In the case of a two-stage heterogeneously catalyzed partial oxidation of propene to acrylic acid, appropriately in application terms, a second two-zone process stage for the heterogeneously catalyzed partial gas phase oxidation of acrolein to acrylic acid will be connected downstream of the inventive process stage, and will be operated as described in WO 2007/082827.

Of course, it is possible to combine two two-zone tube bundle reactors connected in series to give a four-zone tube bundle reactor, as described by WO 01/36364 (cf. also WO 2007/082827, page 51).

For experimental determination of the effective temperature of the fixed catalyst bed in a reaction tube of a tube bundle reactor, it may have a thermowell running through the center of the reaction tube from the top downward, in which, with the aid of thermocouples run within the thermowell, the effective fixed catalyst bed temperature (the reaction temperature) can be determined over the entire reaction tube length. In principle, every reaction tube present in a tube bundle reactor and charged with the fixed catalyst bed could be equipped as described above.

Appropriately in application terms, however, a tube bundle reactor has only a limited number of such thermal reaction tubes, or else merely "thermal tubes" for short (cf., for example, page 56 of WO 2007/082827, EP-A 873783, EP-A 1270065 and U.S. Pat. No. 7,534,339 B2).

Since thermal tubes, in addition to the fixed catalyst bed, also have to accommodate the thermowells, in the case of otherwise identical tube configuration, they would have an equal heat exchange surface area but a lower free cross section which can be occupied by the fixed catalyst bed than a mere "reaction tube". This is taken into account by the fact that they (the thermal tubes) are configured such that the ratio of free cross-sectional area in the tube to the circumference of the tube is the same for thermal tube and reaction tube. Otherwise, reaction tube and thermal tube, with identical tube length, each have the same fixed catalyst bed structure over their tube length. When charging with fixed catalyst bed, it should additionally be ensured that the profile of the pressure drop profile established in each case over the tube length in the course of flow of reaction gas mixture through reaction tube or thermal tube is configured homogeneously in both tube types. Influence can be exercised in a corresponding manner via the rate of filling of the tubes with the shaped bodies and/or by additional use of comminuted (spalled) shaped bodies (cf., for example, EP-A 873783 and U.S. Pat. No. 7,534,339 B2). Overall, it is ensured in this way that a thermal tube and a reaction tube have equal ratios of evolution of heat of reaction in the tube interior and removal of heat of reaction from the tube interior along the entire tube length. The thermal tube is thus capable of representing the profile of the effective fixed catalyst bed temperature in the reaction tube for many reaction tubes.

Generally, it is favorable to operate an inventive partial oxidation of propene to acrolein such that the propene content in the product gas mixture of this partial oxidation does riot exceed the value of 10000 ppm by weight, preferably 6000 ppm by weight and more preferably 4000 to 2000 ppm by weight.

The propene content in the reaction gas input mixture in the process according to the invention may, for example, be at values of 2 to 25% by volume, often 3 to 20% by volume, or 4 to 15% by volume, frequently 5 to 12% by volume or 6 to 8% by volume (based in each case on the total volume). Suitable propene sources are especially "polymer-grade propene" and "chemical-grade propene" according to WO 2004/009525.

Frequently, the propene→acrolein process according to the invention will be carried out at a propene:oxygen:inert gases (including steam) volume ratio in the reaction gas input mixture of 1:(1.0 to 3.0):(5 to 25), preferably 1:(1.7 to 2.3): (10 to 15). In general, the inert gas will consist to an extent of at least 20% of its volume of molecular nitrogen. However, t may also consist to an extent of ≥30% by volume, Or to an extent of ≥40% by volume, or to an extent of ≥50% by volume, or to an extent of ≥60% by volume, or to an extent of ≥70% by volume, or to an extent of ≥80% by volume, or to an extent of ≥90% by volume, or to an extent of ≥95% by volume of molecular nitrogen (possible inert gases, in addition to molecular nitrogen, are, for example, gases such as propane, ethane, methane, pentane, butane, $CO_2$, CO, steam and/or noble gases). Of course, the inert diluent gas in an inventive propene partial oxidation to acrolein may also consist to an extent of up to 50 mol %, or up to 75 mol % or more of propane (for example, useful reaction gas input mixtures for the process according to the invention include all of those for the propene partial oxidation to acrolein disclosed in documents WO 2007/13504, WO 2007/060036, WO 2007/042457, WO 2006/002713, WO 2006/002708 and WO 2006/002703). Cycle gas, as remains in the two-stage propene partial oxidation to acrylic acid after removal of the acrylic acid from the product gas mixture may also be part of the diluent gas.

The aforementioned composition ranges also apply to such two-stage processes, both in cases of secondary gas supply (for example supply of air and/or inert gas between the first and second reaction stage) and in cases where no secondary gas is supplied.

Reaction gas input mixtures suitable in accordance with the invention are, for example, those which are composed of
5 to 15% (preferably 6 to 11%) by volume of propene,
0.5 or 4 to 20% (preferably 6 to 12%) by volume of water,
≥0 to 10% (preferably ≥0 to 5%) by volume of constituents other than propene, water, molecular oxygen and molecular nitrogen,
sufficient molecular oxygen that the molar ratio of molecular oxygen present to propene present in the reaction gas input mixture is 1.5 to 2.5 (preferably 1.6 to 2.2), and, as the remainder up to 100% by volume of the total amount, of molecular nitrogen,
as recommended by DE-A 10302715.

Especially at particularly high propene space velocities on the fixed bed catalyst charge, the additional use of inert diluent gases with high specific heat is recommended.

Especially in the case of a two-stage heterogeneously catalyzed gas phase partial oxidation of propene to acrylic acid, in which the process according to the invention forms merely the first reaction stage, the following conditions of the reaction gas input mixture are also useful. For example, the reaction gas input mixture may comprise ≥0.01% by volume, or ≥0.1% by volume, or ≥0.5% by volume, or ≥2% by volume of $CO_2$. Usually, the aforementioned $CO_2$ content will be ≤25% by volume.

Especially when the source used for the molecular oxygen in the process according to the invention is air, the reaction gas input mixture will comprise molecular nitrogen as a further inert diluent gas. In principle, the reaction gas input mixture in the process according to the invention may comprise ≥1% by volume, or ≥5% by volume, or ≥10% by volume, or ≥20% by volume, or ≥30% by volume, or ≥40% by volume of molecular nitrogen. However, the content in the reaction gas input mixture of molecular nitrogen will generally be at values of ≤80 mol %, or ≤70 mol %, or ≤60 mol %.

The reaction gas input mixture may also (as already stated) comprise propane as an inert diluent gas. This propane content of the reaction gas input mixture may be up to 70% by volume (for example 5 to 70% by volume), or up to 60% by volume, or up to 50% by volume, or up to 40% by volume, or to 30% by volume, or to 20% by volume, or up to 10% by volume. Frequently, this propane content will be ≥0.5 or ≥1% by volume. However, it may also be at values of ≥0.01% by volume, or ≥0.02% by volume, or ≥0.03% by volume. In general, the reaction gas input mixture comprises ≤10% by volume, in many cases ≤5% by volume of propane.

In the process according to the invention, this propane may be added, for example, deliberately as an inert diluent gas to be supplied separately to the reaction gas input mixture However, it will be appreciated that the propane may also be part of the reaction gas input mixture by virtue of a partial dehydrogenation or oxidehydrogenation of propane functioning as the propene source therefor (generally, these are effected under heterogeneous catalysis). In other words, the propene present in the reaction gas input mixture may be supplied to the reaction gas input mixture at least partly with accompaniment by unconverted propane from a partial dehydrogenation (for example homogeneously and/or heterogeneously catalyzed, in the presence and/or with exclusion of molecular oxygen).

The process according to the invention comprises in particular also those embodiments in which the reaction gas input mixture comprises >0 to 35% by volume, frequently 1 to 25% by volume, or 5 to 15% by volume, or to 10% by volume, of $H_2O$.

Typical reaction gas input mixtures are, for example, those which comprise:
5 or 6 to 11% by volume of propene,
2 or 6 to 12% by volume of water,
>0, frequently ≥0.5 or ≥1 to 10% by volume of propane,
≥0 to 5% by volume of constituents other than propene, propane, water, oxygen and nitrogen,
sufficient molecular oxygen that the molar ratio of molecular oxygen present to propene present is 1 to 3, and,
as the remainder up to 100% by volume of the total amount of molecular nitrogen.

Inventive reaction gas input mixtures may also comprise:
6 to 9% by volume of propene,
8 to 18% by volume of molecular oxygen,
6 to 30 or to 35% by volume of propane and
32 to 72% by volume of molecular nitrogen.

Inventive reaction gas input mixtures may also comprise up to 20% by volume of $H_2$.

In other words, reaction gas input mixtures of the process according to the invention may also comprise:
4 to 25% by volume of propene,
6 to 70% by volume of propane,
5 to 60% by volume of $H_2O$,
8 to 65% by volume of $O_2$ and
0.3 to 20% by volume of $H_2$.

However, the process according to the invention is also favorable when the reaction gas input mixture comprises 0.1 to 30% by volume of $CO_2$.

For all aforementioned arrangements of the process according to the invention, a second reaction stage of the heterogeneously catalyzed partial gas phase oxidation of acrolein to acrylic acid may in each case follow the process according to the invention.

At this point, it should be mentioned once again that a portion of the reaction gas input mixture may be what is called cycle gas. This is gas which remains, for example, in a two-stage partial oxidation of propene to acrylic acid after the product removal (acrylic acid removal) from the product gas mixture of the second stage, and, in the case of a series connection of the two stages, is generally partly recycled as inert diluent gas to charge the first and/or second stage.

Typical cycle gas contents are:
0-0.1% by volume of others, for example diphenyl, diphenyl ether and/or dimethyl phthalate,
0-0.1% by volume of acrylic acid,
0-0.1% by volume of acrolein,
2-5% by volume of oxygen,
0.5-5% by volume of steam,
0-3% by volume of carbon monoxide,
0-8% by volume of carbon dioxide,
0-2% by volume of propane,
0.05-0.5% by volume of propene,
85-95% by volume of nitrogen.

The acrylic acid can be removed, for example, as described in EP-A 982 287, EP-A 982 289, DE-A 199 24 532, DE-A 101 15 277, DE-A 196 06 877, DE-A 197 40 252, DE-A 196 27 847, DE-A 100 53 086, EP-A 982 288 and DE-A 196 27 847.

Otherwise, configurations of a two-zone tube bundle reactor particularly favorable for the process according to the invention are described on pages 56 ff. of WO 2007/082827 (including corresponding fixed catalyst bed charge of the reaction tubes).

The present patent application thus comprises especially the following inventive embodiments:

1. A process for long-term operation of a heterogeneously catalyzed partial gas phase oxidation of propene to acrolein, in which a reaction gas input mixture which comprises propene, molecular oxygen and at least one inert gas and comprises the molecular oxygen and the propene in a molar $O_2:C_3H_6$ ratio of ≥1 is conducted through a fixed catalyst bed whose active material is at least one multimetal oxide comprising the elements Mo, Fe and Bi, with the proviso that
    the fixed catalyst bed is arranged in two spatially successive temperature zones A, B,
    both the temperature $T^A$ of temperature zone A and the temperature $T^B$ of temperature zone B are a temperature in the temperature range from 280 to 420° C.,
    the reaction gas input mixture flows through temperature zones A, B in the time sequence "first A" and "then B", temperature zone A extending up to a conversion $C^A$ of the propene present in the reaction gas input mixture in the range from 45 to 85 mol %, and the conversion of the propene increasing in temperature zone B to a value $C^B$ of ≥90 mol %,
    in single pass of the reaction gas input mixture through the overall fixed catalyst bed, the selectivity of acrolein formation, based on propene converted, is ≥80 mol %,
    the space velocity of propene present in the reaction gas input mixture on the fixed catalyst bed is ≥140 l (STP) of propene/l of fixed catalyst bed·h,
    the temperatures $T^A$ and $T^B$ on completion of fresh charging of the fixed catalyst bed are such that the difference $\Delta T^{BA}=T^B-T^A>0°$ C.,
    then, with increasing operating time, in order to counteract the reduction in the quality of the fixed catalyst bed, at least one of the two temperatures $T^A$, $T^B$ is increased, wherein
    the increasing of the at least one of the two temperatures $T^A$, $T^B$ is undertaken such that the difference $\Delta T^{BA}=T^B-T^A$ increases with increasing operating time.

2. The process according to embodiment 1, wherein, on completion of fresh charging of the fixed catalyst bed, $\Delta T^{BA} \geq 2°$ C.

3. The process according to embodiment 1, wherein, on completion of fresh charging of the fixed catalyst bed, $\Delta T^{BA} \geq 3°$ C.

4. The process according to embodiment 1, wherein, on completion of fresh charging of the fixed catalyst bed, $\Delta T^{BA} \geq 5°$ C.

5. The process according to any of embodiments 1 to 4, wherein, on completion of fresh charging of the fixed catalyst bed, $\Delta T^{BA} \leq 50°$ C.

6. The process according to any of embodiments 1 to 4, wherein, on completion of fresh charging of the fixed catalyst bed, $\Delta T^{BA} \leq 40°$ C.

7. The process according to embodiment 1, wherein, on completion of fresh charging of the fixed catalyst bed, $\Delta T^{BA}$ is ≥5° C. and ≤35° C.

8. The process according to embodiment 1, wherein, on completion of fresh charging of the fixed catalyst bed, $\Delta T^{BA}$ is $\geq 5°$ C. and $\leq 30°$ C.

9. The process according to embodiment 1, wherein, on completion of fresh charging of the fixed catalyst bed, $\Delta T^{BA}$ is $\geq 10°$ C. and $\leq 25°$ C.

10. The process according to any of embodiments 1 to 9, wherein, on completion of fresh charging of the fixed catalyst bed, the difference between the maximum reaction temperature in temperature zone A, $T^{maxA}$, and the maximum reaction temperature in temperature zone B, $T^{maxB}$, formed as $T^{maxA} - T^{maxB}$, is $\geq 0°$ C. and $\leq 80°$ C.

11. The process according to embodiment 10, wherein $T^{maxA} - T^{maxB}$ is $\geq 0°$ C. and $\leq 70°$ C.

12. The process according to embodiment 10, wherein $T^{maxA} - T^{maxB}$ is $\geq 2°$ C. and $\leq 40°$ C.

13. The process according to embodiment 10, wherein $T^{maxA} - T^{maxB}$ is $\geq 5°$ C. and $\leq 25°$ C.

14. The process according to embodiment 10, wherein $T^{maxA} - T^{maxB}$ is $\geq 10°$ C. and $\leq 25°$ C.

15. The process according to any of embodiments 1 to 14, wherein both $T^B$ and $T^A$ are increased in long-term operation.

16. The process according to embodiment 15, wherein, based on the same operating time in long-term operation, the increase in $T^B$ is 1.2 to 5 times the increase in $T^A$.

17. The process according to embodiment 15, wherein, based on the same operating time in long-term operation, the increase in $T^B$ is 1.5 to 3 times the increase in $T^A$.

18. The process according to embodiment 15, wherein, based on the same operating time in long-term operation, the increase in $T^B$ is 1.5 to 2.5 times the increase in $T^A$.

19. The process according to any of embodiments 1 to 18, wherein the difference between the maximum reaction temperature in temperature zone A, $T^{maxA}$, and the maximum reaction temperature in temperature zone B, $T^{maxB}$, formed as $T^{maxA} - T^{maxB}$, is reduced with increasing operating time, but does not become negative.

20. The process according to any of embodiments 1 to 19, wherein the operating time extends to at least 6 months.

21. The process according to any of embodiments 1 to 19, wherein the operating time extends to at least 12 months.

22. The process according to any of embodiments 1 to 19, wherein the operating time extends to at least 18 months.

23. The process according to any of embodiments 1 to 19, wherein the operating time extends to at least 24 months.

24. The process according to any of embodiments 1 to 19, wherein the operating time extends to at least 36 months.

25. The process according to any of embodiments 1 to 24, wherein $\Delta T^{BA}$ does not exceed 70° C. with increasing operating time.

26. The process according to embodiment 25, wherein $\Delta T^{BA}$ does not exceed 60° C. with increasing operating time.

27. The process according to embodiment 25, wherein $\Delta T^{BA}$ does not exceed 50° C. with increasing operating time.

28. The process according to embodiment 25, wherein $\Delta T^{BA}$ does not exceed 40° C. with increasing operating time.

29. The process according to any of embodiments 1 to 28, wherein $T^A$ is within the range from 300 to 400° C. over the entire operating time.

30. The process according to any of embodiments 1 to 28, wherein $T^A$ is within the range from 310 to 390° C. over the entire operating time.

31. The process according to any of embodiments 1 to 28, wherein $T^A$ is within the range from 320 to 380° C. over the entire operating time.

32. The process according to any of embodiments 1 to 31, wherein $T^B$ is within the range from 305 to 415° C. over the entire operating time.

33. The process according to any of embodiments 1 to 31, wherein $T^B$ is within the range from 315 to 410° C. over the entire operating time.

34. The process according to any of embodiments 1 to 31, wherein $T^B$ is within the range from 330 to 410° C. over the entire operating time.

35. The process according to any of embodiments 1 to 34, wherein temperature zone A extends up to a conversion $C^A$ of the propene present in the reaction gas input mixture in the range from 50 to 80 mol %.

36. The process according to any of embodiments 1 to 34, wherein temperature zone A extends up to a conversion $C^A$ of the propene present in the reaction gas input mixture in the range from 55 to 75 mol %.

37. The process according to any of embodiments 1 to 36, wherein the conversion of the propene in temperature zone B increases to a value of $\geq 92$ mol %.

38. The process according to any of embodiments 1 to 36, wherein the conversion of the propene in temperature zone B increases to a value of $\geq 94$ mol %.

39. The process according to any of embodiments 1 to 36, wherein the conversion of the propene in temperature zone B increases to a value of $\geq 96$ mol %.

40. The process according to any of embodiments 1 to 39, wherein the selectivity of acrolein formation in single pass of the reaction gas input mixture through the entire fixed catalyst bed and based on propene converted is $\geq 85$ mol % or $\geq 89$ mol %.

41. The process according to any of embodiments 1 to 40, wherein the space velocity of propene on the fixed catalyst bed is $\geq 150$ l (STP)/l·h.

42. The process according to any of embodiments 1 to 40, wherein the space velocity of propene on the fixed catalyst bed is $\geq 160$ l (STP)/l·h.

43. The process according to any of embodiments 1 to 40, wherein the space velocity of propene on the fixed catalyst bed is $\geq 170$ l (STP)/l·h.

44. The process according to any of embodiments 1 to 40, wherein the space velocity of propene on the fixed catalyst bed is $\geq 180$ l (STP)/l·h.

45. The process according to any of embodiments 1 to 44, wherein the space velocity of propene on the fixed catalyst bed is $\leq 400$ l (STP)/l·h.

46. The process according to any of embodiments 1 to 44, wherein the space velocity of propene on the fixed catalyst bed is $\leq 300$ l (STP)/l·h.

47. The process according to any of embodiments 1 to 44, wherein the space velocity of propene on the fixed catalyst bed is $\leq 250$ l (STP)/l·h.

48. The process according to any of embodiments 1 to 47, wherein the fixed catalyst bed is present in the reaction tubes of a tube bundle reactor having two temperature zones.

49. The process according to any of embodiments 1 to 48, wherein the long-term operation is interrupted and the fixed catalyst bed is regenerated by passing a hot gas mixture of molecular oxygen and inert gas through the fixed catalyst bed, and then the long-term operation is continued.

50. The process according to any of embodiments 1 to 49, wherein the reaction gas input mixture comprises 2 to 25% by volume of propene.

51. The process according to any of embodiments 1 to 49, wherein the reaction gas input mixture comprises 4 to 15% by volume of propene.

52. The process according to any of embodiments 1 to 49, wherein the reaction gas input mixture comprises 5 to 12% by volume of propene.
53. The process according to any of embodiments 1 to 52, wherein the at least one inert gas consists of molecular nitrogen to an extent of at least 40% of its volume.
54. The process according to any of embodiments 1 to 52, wherein the at least one inert gas consists of n-propane to an extent of up to 50% of its volume.
55. The process according to any of embodiments 1 to 49, wherein the reaction gas input mixture is composed to an extent of
   5 to 15% by volume of propene,
   0.5 to 20% by volume of water,
   ≥0 to 10% by volume of constituents other than propene, water, molecular oxygen and molecular nitrogen,
   sufficient molecular oxygen that the molar ratio of molecular oxygen present in the reaction gas input mixture to propene present therein is 1.5 to 2.5, and
   as the remainder up to 100% by volume of the total amount, of molecular oxygen.
56. The process according to any of embodiments 1 to 54, wherein the reaction gas input mixture comprises the molecular oxygen and the propene in a molar $O_2:C_3H_6$ ratio of ≤3.
57. The process according to any of embodiments 1 to 54, wherein the reaction gas input mixture comprises the molecular oxygen and the propene in a molar $O_2:C_3H_6$ ratio of ≥1.2 and ≤3.
58. The process according to any of embodiments 1 to 57, wherein the active material of the fixed catalyst bed is at least one multimetal oxide comprising the elements Mo, Fe and Bi, and additionally at least one of the two elements Ni and Co.
59. The process according to embodiment 58, wherein, of the five elements Mo, Fe, Bi, Ni and Co, based on the total molar amount thereof present in the active material, the element Mo accounts for the greatest molar proportion in mol % based on the total molar amount G.
60. The process according to any of embodiments 1 to 57, wherein the active material is at least one multimetal oxide active material of the general formula I $$Mo_{12}Bi_aFe_bX^1_cX^2_dX^3_eX^4_fO_n \qquad (I),$$

in which the variables are each defined as follows:
   $X^1$=nickel and/or cobalt,
   $X^2$=thallium, an alkali metal and/or an alkaline earth metal,
   $X^3$=zinc, phosphorus, arsenic, boron, antimony, tin, cerium, lead and/or tungsten,
   $X^4$=silicon, aluminum, titanium and/or zirconium,
   a=0.5 to 5,
   b=0.01 to 5,
   c=0 to 10,
   d=0 to 2,
   e=0 to 8,
   f=0 to 10 and
   n=a number which is determined by the valency and frequency of the elements in I other than oxygen.
61. The process according to embodiment 60, wherein the stoichiometric coefficient b is 2 to 4.
62. The process according to embodiment 60 or 61, wherein the stoichiometric coefficient c is 3 to 10.
63. The process according to either of embodiments 60 and 61, wherein the stoichiometric coefficient d is 0.02 to 2.
64. The process according to any of embodiments 1 to 63, wherein $\Delta T^{BA}$ increases by at least 5° C. with increasing operating time.
65. The process according to any of embodiments 1 to 63, wherein $\Delta T^{BA}$ increases by at least 10° C. with increasing operating time.
66. The process according to any of embodiments 1 to 65, wherein $\Delta T^{BA}$ increases by not more than 30° C. with increasing operating time.
67. The process according to any of embodiments 1 to 65, wherein $\Delta T^{BA}$ increases by not more than 20° C. with increasing operating time.
68. The process according to any of embodiments 1 to 67, wherein the maximum reaction temperature in reaction zone A, $T^{maxA}$, does not exceed 420° C. with increasing operating time.
69. The process according to any of embodiments 1 to 67, wherein the maximum reaction temperature in reaction zone A, $T^{maxA}$, does not exceed 410° C. with increasing operating time.
70. The process according to any of embodiments 1 to 69, wherein the maximum reaction temperature in reaction zone A, $T^{maxA}$, is ≥350° C.
71. The process according to any of embodiments 1 to 69, wherein the maximum reaction temperature in reaction zone A, $T^{maxA}$, is ≥370° C.
72. The process according to any of embodiments 1 to 71, wherein the difference between the maximum reaction temperature in temperature zone A, $T^{maxA}$, and the temperature $T^A$ of temperature zone A, formed as $\Delta T^{HB}_A = T^{maxA} - T^A$, is 40 to 90° C.
73. The process according to any of embodiments 1 to 72, wherein the fixed catalyst bed is present in the tubes of a tube bundle reactor having two temperature zones, a salt melt flowing through each temperature zone and the heat transfer from the tube wall to the salt melt being ≥1000 W/m²·K and ≤3000 W/m²·K.
74. The process according to any of embodiments 1 to 72, wherein the fixed catalyst bed is present in the tubes of a tube bundle reactor having two temperature zones, a salt melt flowing through each temperature zone and the heat transfer from the tube wall to the salt melt being ≥1500 W/m²·K and ≤3000 W/m²·K.
75. The process according to any of embodiments 1 to 72, wherein the fixed catalyst bed is present in the tubes of a tube bundle reactor having two temperature zones, a salt melt flowing through each temperature zone and the heat transfer from the tube wall to the salt melt being ≥2000 W/m²·K and ≤3000 W/m²·K.

EXAMPLE AND COMPARATIVE EXAMPLE

I. Example

A thermal reaction tube (V2A steel; external diameter 33.7 mm, wall thickness 2 mm, internal diameter 29.7 mm, length: 350 cm, and a thermal protection tube (thermowell) running through the center of the thermal tube from the top downward for accommodating a thermocouple with which the reaction temperature (the effective fixed catalyst bed temperature) was determinable over the entire tube length) was charged from the top downward as follows:

Section 1: length 50 cm
   steatite rings of geometry 7 mm×7 mm×4 mm (external diameter×length×internal diameter, C220 steatite from CeramTec) as a preliminary bed.
Section 2: length 140 cm
   catalyst charge with a homogeneous mixture consisting of 30% by weight of steatite rings of geometry 5 mm×3 mm×2 mm (external diameter×length×internal diameter; C220 steatite from CeramTec), 55% by weight of unsupported catalyst from section 3 and 15% by weight of spalled unsupported catalyst from section 3.

Section 3: length 160 cm catalyst charge with a homogeneous mixture of 85% by weight of the annular unsupported catalyst I (5 mm×3 mm×2 mm=external diameter×length×internal diameter) according to the working example of DE-A 102009047291 with the stoichiometry $[Bi_2W_2O_9 \cdot 2WO_3]_{0.40}[Mo_{12}Co_{5.4}Fe_{3.1}Si_{1.5}K_{0.08}O_x]_1$, and 15% by weight of spall of the aforementioned unsupported catalyst.

The thermal reaction tube is supposed to reflect the behavior of a simple reaction tube made of corresponding material with identical tube length, the internal diameter of which is 26 mm with wall thickness 2 mm, and which is charged in a corresponding manner to the thermal reaction tube, except that the proportion by weight of unsupported catalyst rings which is spelled in each case in the particular section in the case of the thermal reaction tube unspalled in the simple reaction tube, i.e. forms part of the charge in ring form.

From the top downward, the first 175 cm of the thermal reaction tube were thermostatted by means of a salt bath A pumped in countercurrent to the reaction mixture over the 175 cm, which was supplied with the temperature $T^A$. The second 175 were thermostatted by means of a salt bath B pumped in countercurrent in a corresponding manner, which was supplied with the temperature $T^B$. Over the particular temperature zone, the particular salt bath temperature was essentially constant.

The two salt baths A, B each consisted of 53% by weight of potassium nitrate, 40% by weight of sodium nitrite and 7% by weight of sodium nitrate. In the two tube sections, each of length 175 cm, the flow toward the reaction tube was essentially vertical with respect to the flow direction of the reaction gas. The flow rate of the two salt melts was such that a further increase essentially did not bring about any improvement in the heat transfer from the thermal tube interior into the salt bath (cf. EP-A1547994).

The thermal tube charged as described above was charged in steady-state operation with a reaction gas input mixture which had the following contents and was obtained from air (as the oxygen source), chemical-grade propene and cycle gas:

6 to 6.5% by vol. of propene
0.7 to 1.2% by vol. of $H_2O$,
0.4 to 0.6% by vol. of CO,
0.7 to 1.1% by vol. of $CO_2$,
0.01 to 0.04% by vol. of acrolein,
0.005 to 0.015% by vol. of ethene,
0.025 to 0.035% by vol. of propane,
10.8 to 11.7% by vol. of $O_2$ and
at least 77% by vol. of $N_2$.

The space velocity of propene present in the reaction gas input mixture on the fixed catalyst bed was always within the range of 185±10 l (STP)/l·h during the steady-state operating phases. The pressure at the inlet of the thermal reaction tube was essentially 2.0 atm.

During a steady-state operating phase, the temperatures $T^A$, $T^B$ were each kept constant.

A steady-state operating phase extended over 24 operating days. At the end of each steady-state operating phase, the partial oxidation process was interrupted and the fixed catalyst bed was regenerated as described in WO 2004/085369.

To restart the partial oxidation process on completion of regeneration of the fixed catalyst bed, and for the first startup of the fixed catalyst bed, the contents of the reaction gas input mixture were changed to the following values:

5.7 to 6.2% by vol. of propene
0.7 to 1.2% by vol. of $H_2O$,
0.4 to 0.6% by vol. of CO,
0.7 to 1.1% by vol. of $CO_2$,
0.01 to 0.04% by vol. of acrolein,
0.005 to 0.015% by vol. of ethene,
0.025 to 0.035% by vol. of propane,
10.3 to 11.2% by vol. of $O_2$ and
at least 78.5% by vol. of $N_2$.

In addition, for a restart and for the first startup, the propene space velocity on the fixed catalyst bed was lowered to 100 l (STP)/l·h, and $T^A$, $T^B$ were restricted, with the proviso that $\Delta T^{BA} \geq 0$, to such an extent that the propene conversion based on a single pass of the reaction gas mixture through the thermal tube was limited to 94 mol %. Proceeding from these operating conditions, the operating conditions of the steady-state operation were controlled such that $T^{maxA}$ was always > than $T^{maxB}$ and always less than the $T^{maxA}$ in the subsequent steady-state operation.

Table 1 below shows the resulting values for $T^{maxA}$ and for the overall selectivity $S^{AC+AA}$ of the formation of acrolein and acrylic acid (the selectivity of overall target product formation based on propene converted in single pass of the reaction gas mixture through the thermal tube (thermal reaction tube)) as a function of $T^A$ and $T^B$ for the particular steady-state operating phase at the particular propene space velocity PSV on the fixed catalyst bed. In addition, table 1 shows the values for $\Delta T^{BA}$ and for $\Delta T^{HB}_A$. All figures relate to the 24$^{th}$ operating day of the particular steady-state operating phase.

II. Comparative Example

Everything in the comparative example was performed as in the example, except with the difference that, in long-term operation, to maintain the propene conversion, $T^A$, $T^B$ were altered such that $\Delta T^{BA}$ was reduced according to the teaching of WO 2007/082827. Table 2 shows the results in a manner corresponding to that of table 1 for the example.

TABLE 1

(example):

| Operating phase | PSV (l (STP)/l · h) | $T^A$ (° C.) | $T^B$ (° C.) | $T^{maxA}$ (° C.) | $\Delta T^{BA}$ (° C.) | $\Delta T^{HB}_A$ (° C.) | $S^{AC+AA}$ (mol %) |
|---|---|---|---|---|---|---|---|
| 1 | 180 | 325 | 341 | 385 | 16 | 60 | 95.5 |
| 2 | 175 | 325 | 342 | 384 | 17 | 59 | 96.2 |
| 3 | 175 | 325 | 343 | 384 | 18 | 59 | 96.5 |
| 4 | 190 | 327 | 346 | 385 | 19 | 58 | 96.1 |
| 5 | 179 | 328 | 347 | 386 | 19 | 58 | 96.1 |
| 6 | 182 | 329 | 348 | 392 | 19 | 63 | 96.2 |
| 7 | 175 | 330 | 349 | 394 | 19 | 64 | 96.3 |
| 8 | 192 | 333 | 353 | 396 | 20 | 62 | 96.5 |
| 9 | 192 | 333 | 355 | 396 | 22 | 63 | 96.3 |
| 10 | 194 | 335 | 357 | 402 | 22 | 67 | 96.5 |
| 11 | 187 | 336 | 359 | 400 | 23 | 64 | 96.5 |
| 12 | 182 | 334 | 357 | 396 | 23 | 62 | 96.5 |
| 13 | 188 | 336 | 360 | 398 | 24 | 62 | 96.5 |
| 14 | 187 | 334 | 358 | 400 | 24 | 66 | 96.3 |
| 15 | 188 | 336 | 361 | 405 | 25 | 69 | 96.6 |
| 16 | 183 | 338 | 363 | 404 | 25 | 66 | 96.3 |
| 17 | 190 | 340 | 365 | 409 | 25 | 69 | 96.1 |
| 18 | 184 | 340 | 368 | 408 | 28 | 68 | 96.4 |
| 19 | 190 | 337 | 365 | 406 | 28 | 69 | 96.4 |
| 20 | 192 | 340 | 369 | 409 | 29 | 69 | 96.4 |
| 22 | 190 | 341 | 370 | 408 | 29 | 67 | 96.3 |
| 23 | 194 | 341 | 370 | 410 | 29 | 69 | 96.4 |
| 24 | 186 | 343 | 373 | 410 | 30 | 67 | 95.8 |
| 25 | 191 | 342 | 372 | 411 | 30 | 69 | 95.9 |

TABLE 1-continued (example):

| Operating phase | PSV (l (STP)/l · h) | $T^A$ (° C.) | $T^B$ (° C.) | $T^{maxA}$ (° C.) | $\Delta T^{BA}$ (° C.) | $\Delta T^{HB}_A$ (° C.) | $S^{AC+AA}$ (mol %) |
|---|---|---|---|---|---|---|---|
| 26 | 195 | 341 | 372 | 408 | 31 | 67 | 95.5 |
| 29 | 185 | 340 | 372 | 402 | 32 | 62 | 95.4 |
| 34 | 191 | 349 | 382 | 411 | 33 | 62 | 94.7 |
| 37 | 189 | 355 | 389 | 415 | 34 | 60 | 92.8 |
| 38 | 194 | 360 | 393 | 418 | 33 | 58 | 92.4 |

After the 38th operating phase, the fixed catalyst bed was exchanged for a fresh fixed catalyst bed.

Up to the end of the 23rd operating phase, the resulting propene conversion based on a single pass of the reaction gas mixture through the thermal tube was 95.1±0.3 mol %. The propene conversion in temperature zone A was in the range from 60 to 72 mol % over the entire operating phases.

At the end of the 38th operating phase, the resulting propene conversion based on a single pass of the reaction gas mixture through the thermal tube was only 91.8 mol %.

$T^{maxB}$ in all operating phases was less than $T^{maxA}$. At the beginning of long-term operation, the difference $T^{maxB} - T^{maxA}$ was 15° C. and decreased to 1.5° C. in the course of the long-term operation. The selectivity of acrolein formation, based on propene converted, was >85 mol % in all operating phases.

TABLE 2

(comparative example):

| Operating phase | PSV (l (STP)/l · h) | $T^A$ (° C.) | $T^B$ (° C.) | $T^{maxA}$ (° C.) | $\Delta T^{BA}$ (° C.) | $\Delta T^{HB}_A$ (° C.) | $S^{AC+AA}$ (mol %) |
|---|---|---|---|---|---|---|---|
| 1 | 188 | 325 | 345 | 387 | 20 | 62 | 95.5 |
| 2 | 185 | 326 | 346 | 394 | 20 | 68 | 96.0 |
| 3 | 194 | 327 | 346 | 396 | 19 | 69 | 96.3 |
| 4 | 191 | 328 | 347 | 396 | 19 | 68 | 96.1 |
| 5 | 189 | 330 | 348 | 401 | 18 | 71 | 96.3 |
| 6 | 183 | 332 | 348 | 402 | 16 | 70 | 96.4 |
| 7 | 195 | 334 | 349 | 404 | 15 | 70 | 96.4 |
| 8 | 190 | 336 | 350 | 407 | 14 | 71 | 96.4 |
| 9 | 191 | 337 | 350 | 409 | 13 | 72 | 96.5 |
| 10 | 190 | 339 | 352 | 411 | 13 | 72 | 96.5 |
| 11 | 188 | 341 | 353 | 412 | 12 | 71 | 96.4 |
| 12 | 188 | 344 | 355 | 417 | 11 | 73 | 96.2 |
| 13 | 194 | 345 | 356 | 415 | 11 | 70 | 95.5 |
| 14 | 195 | 347 | 357 | 415 | 10 | 68 | 94.7 |
| 15 | 189 | 349 | 358 | 415 | 9 | 66 | 93.7 |

After the 15th operating phase, the fixed catalyst bed was exchanged for a fresh fixed catalyst bed. Up to the end of the 12th operating phase, the resulting propene conversion based on a single pass of the reaction gas mixture through the thermal tube was 94.8±0.3 mol %. The propene conversion in temperature zone A was in the range of 65 to 77 mol % over the entire operating phase.

At the end of the 15th operating phase, the resulting propene conversion based on a single pass of the reaction gas mixture through the thermal tube was only 92 mol %.

$T^{maxB}$ in all operating phases was less than $T^{maxA}$.

The selectivity of acrolein formation, based on propene converted, was >85 mol % in all operating phases.

U.S. Provisional Patent Application No. 61/393,370, filed Oct. 15, 2010, is incorporated into the present patent application by literature reference. With regard to the abovementioned teachings, numerous changes and deviations from the present invention are possible. It can therefore be assumed that the invention, within the scope of the appended claims, can be performed differently than the way described specifically herein.

The invention claimed is:

1. A process for the long-term operation of a heterogeneously catalyzed partial gas phase oxidation of propene to acrolein, comprising conducting a reaction gas input mixture which comprises propene, molecular oxygen and at least one inert gas through a fixed catalyst bed whose active material is at least one multimetal oxide comprising the elements Mo, Fe and Bi, with the proviso that:

the reaction gas input mixture comprises the molecular oxygen and the propene in a molar $O_2:C_3H_6$ ratio of ≥1, the fixed catalyst bed is arranged in two spatially successive temperature zones A, B, both the temperature $T^A$ of temperature zone A and the temperature $T^B$ of temperature zone B are a temperature in the temperature range from 280 to 420° C., the reaction gas input mixture flows through temperature zones A, B in the time sequence "first A" and "then B", temperature zone A extending up to a conversion $C^A$ of the propene present in the reaction gas input mixture in the range from 45 to 85 mol %, and the conversion of the propene increasing in temperature zone B to a value $C^B$ of ≥90 mol %, in a single pass of the reaction gas input mixture through the overall fixed catalyst bed, the selectivity of acrolein formation, based on propene converted, is ≥80 mol %, the space velocity of propene present in the reaction gas input mixture on the fixed catalyst bed is ≥140 l (STP) of propene/l of fixed catalyst bed·h, the temperatures $T^A$ and $T^B$ on completion of fresh charging of the fixed catalyst bed are such that the difference $\Delta T^{BA}=T^B-T^A>0°$ C., then, with increasing operating time, in order to counteract the reduction in the quality of the fixed catalyst bed, at least one of the two temperatures $T^A$, $T^B$ is increased, wherein the increasing of the at least one of the two temperatures $T^A$, $T^B$ is undertaken such that the difference $\Delta T^{BA}=T^B-T^A$ increases with increasing operating time.

2. The process according to claim 1, wherein, on completion of fresh charging of the fixed catalyst bed, $\Delta T^{BA} \geq 2°$ C.

3. The process according to claim 1 or 2, wherein, on completion of fresh charging of the fixed catalyst bed, $\Delta T^{BA} \leq 50°$ C.

4. The process according to claim 1, wherein, on completion of fresh charging of the fixed catalyst bed, the difference between the maximum reaction temperature in temperature zone A, $T^{maxA}$, and the maximum reaction temperature in temperature zone B, $T^{maxB}$, formed as $T^{maxA}-T^{maxB}$, is ≥0° C. and ≤80° C.

5. The process according to claim 1, wherein both $T^B$ and $T^A$ are increased in long-term operation.

6. The process according to claim 5, wherein, based on the same operating time in long-term operation, the increase in $T^B$ is 1.2 to 5 times the increase in $T^A$.

7. The process according to claim 1, wherein the difference between the maximum reaction temperature in temperature zone A, $T^{maxA}$, and the maximum reaction temperature in temperature zone B, $T^{maxB}$, formed as $T^{maxA}-T^{maxB}$, is reduced with increasing operating time, but does not become negative.

8. The process according to claim 1, wherein the operating time extends to at least 6 months.

9. The process according to claim 1, wherein $\Delta T^{BA}$ does not exceed 70° C. with increasing operating time.

10. The process according to claim 1, wherein $T^A$ is within the range from 300 to 400° C. over the entire operating time.

11. The process according to claim 1, wherein $T^B$ is within the range from 305 to 415° C. over the entire operating time.

12. The process according to claim 1, wherein the fixed catalyst bed is present in the reaction tubes of a tube bundle reactor having two temperature zones.

13. The process according to claim 1, wherein the long-term operation is interrupted and the fixed catalyst bed is regenerated by passing a hot gas mixture of molecular oxygen and inert gas through the fixed catalyst bed, and then the long-term operation is continued.

14. The process according to claim 1, wherein the reaction gas input mixture comprises 2 to 25% by volume of propene.

15. The process according to claim 1, wherein the at least one inert gas consists of molecular nitrogen to an extent of at least 40% of its volume.

16. The process according to claim 1, wherein the reaction gas input mixture comprises the molecular oxygen and the propene in a molar $O_2:C_3H_6$ ratio of $\leq 3$.

17. The process according to claim 1, wherein $\Delta T^{BA}$ increases by at least 5° C. with increasing operating time.

18. The process according to claim 1, wherein the maximum reaction temperature in reaction zone A, $T^{maxA}$, does not exceed 420° C. with increasing operating time.

19. The process according to claim 1, wherein the maximum reaction temperature in reaction zone A, $T^{maxA}$, is $\geq 350°$ C.

20. The process according to claim 1, wherein the difference between the maximum reaction temperature in temperature zone A, $T^{maxA}$, and the temperature $T^A$ of temperature zone A, formed as $\Delta T^{HB}_A = T^{maxA} - T^A$, is 40 to 90° C.

* * * * *